(12) United States Patent
Goodbread et al.

(10) Patent No.: US 9,518,906 B2
(45) Date of Patent: Dec. 13, 2016

(54) COUPLED TORSIONAL RESONATORS VISCOMETER

(75) Inventors: Joseph H. Goodbread, Portland, OR (US); Juerg Dual, Zumikon (CH)

(73) Assignee: BAKER HUGHES INCORPORATED, Houston, TX (US)

( * ) Notice: Subject to any disclaimer, the term of this patent is extended or adjusted under 35 U.S.C. 154(b) by 809 days.

(21) Appl. No.: 13/809,622

(22) PCT Filed: Jul. 20, 2011

(86) PCT No.: PCT/US2011/044645
§ 371 (c)(1),
(2), (4) Date: Feb. 14, 2013

(87) PCT Pub. No.: WO2012/012508
PCT Pub. Date: Jan. 26, 2012

(65) Prior Publication Data
US 2013/0139576 A1    Jun. 6, 2013

Related U.S. Application Data

(60) Provisional application No. 61/422,219, filed on Dec. 13, 2010, provisional application No. 61/380,706, (Continued)

(51) Int. Cl.
*G01N 11/16* (2006.01)
*G01N 29/02* (2006.01)
*G01N 9/00* (2006.01)

(52) U.S. Cl.
CPC ............ *G01N 11/16* (2013.01); *G01N 9/002* (2013.01); *G01N 11/162* (2013.01); *G01N 29/02* (2013.01); *G01N 2009/006* (2013.01)

(58) Field of Classification Search
CPC  G01N 9/001; G01N 2009/006; G01N 11/162; G01N 11/16
See application file for complete search history.

(56) References Cited

U.S. PATENT DOCUMENTS 3,666,974 A * 5/1972 Dostal .................. G04B 17/10
310/25
4,644,803 A * 2/1987 Ward .................... G01N 9/002
177/208

(Continued)

FOREIGN PATENT DOCUMENTS

GB        2114745 A * 8/1983

OTHER PUBLICATIONS

PCT/US2011/044645—International Search Report dated Mar. 5, 2012.

*Primary Examiner* — Paul West
(74) *Attorney, Agent, or Firm* — Mossman, Kumar & Tyler PC

(57) ABSTRACT

A method for measuring the properties of a fluid that uses a torsionally resonant structure having a base structure; at least two parallel tines affixed to the base structure and projecting in the same direction from the base structure; and wherein the base structure is sufficiently compliant as to mutually couple the tines so that they behave as a single resonator when the tines are driven in synchronized manner. The torsionally resonant structure is immersed in the fluid to be measured and a tine driving mechanism is used to drive the tines torsionally. A tine movement sensing mechanism form measurements of tine movement response to the driving mechanism and the measurements of tine movement to form measurements of fluid properties.

37 Claims, 21 Drawing Sheets

Related U.S. Application Data filed on Sep. 7, 2010, provisional application No. 61/366,161, filed on Jul. 21, 2010.

(56) References Cited

U.S. PATENT DOCUMENTS

| | | | |
|---|---|---|---|
| 4,897,541 A * | 1/1990 | Phillips | G01D 5/268 250/227.21 |
| 2005/0262944 A1 | 12/2005 | Bennett et al. | |
| 2006/0218996 A1 | 10/2006 | Matsiev et al. | |
| 2007/0062260 A1 | 3/2007 | Wenger et al. | |

\* cited by examiner

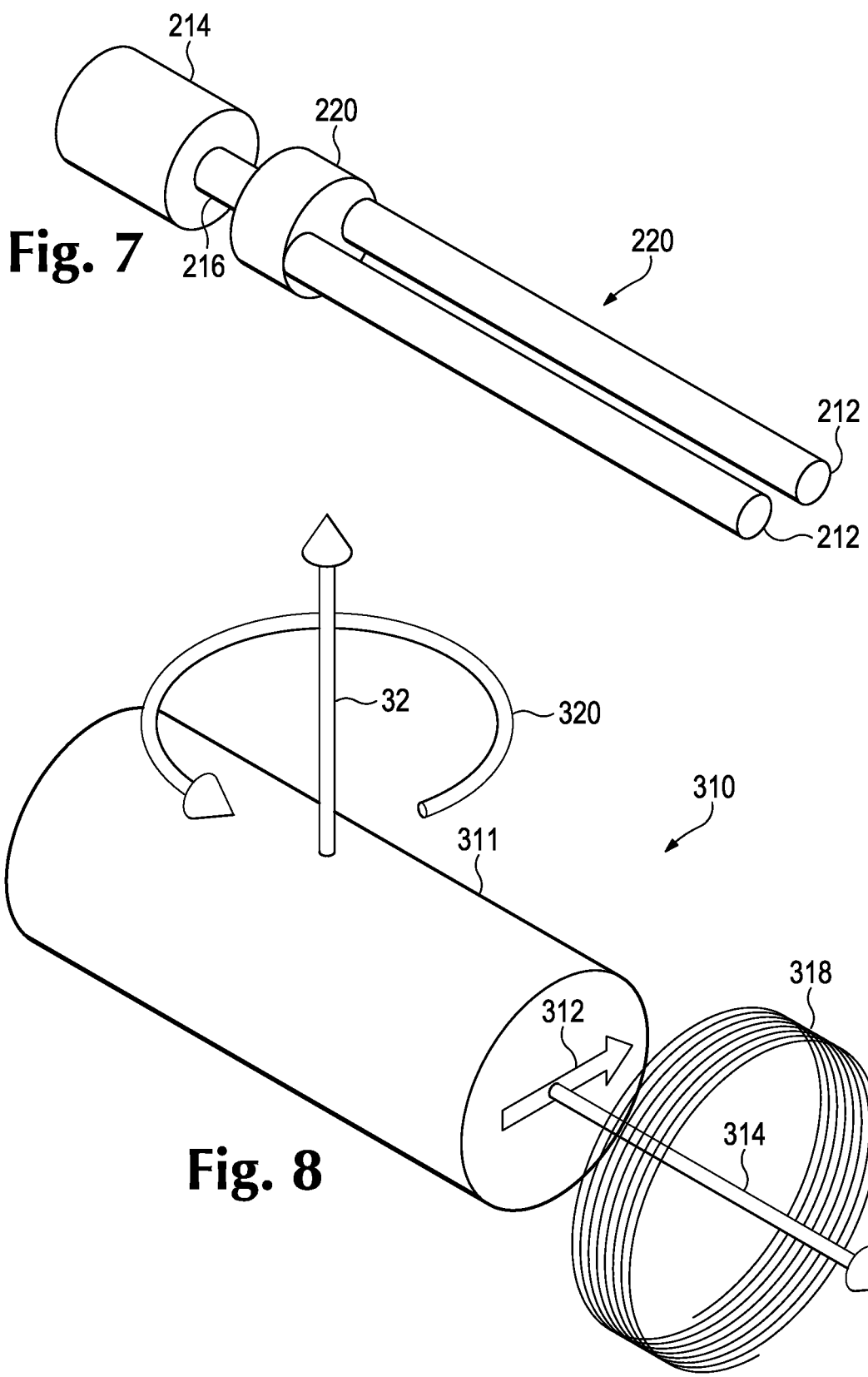

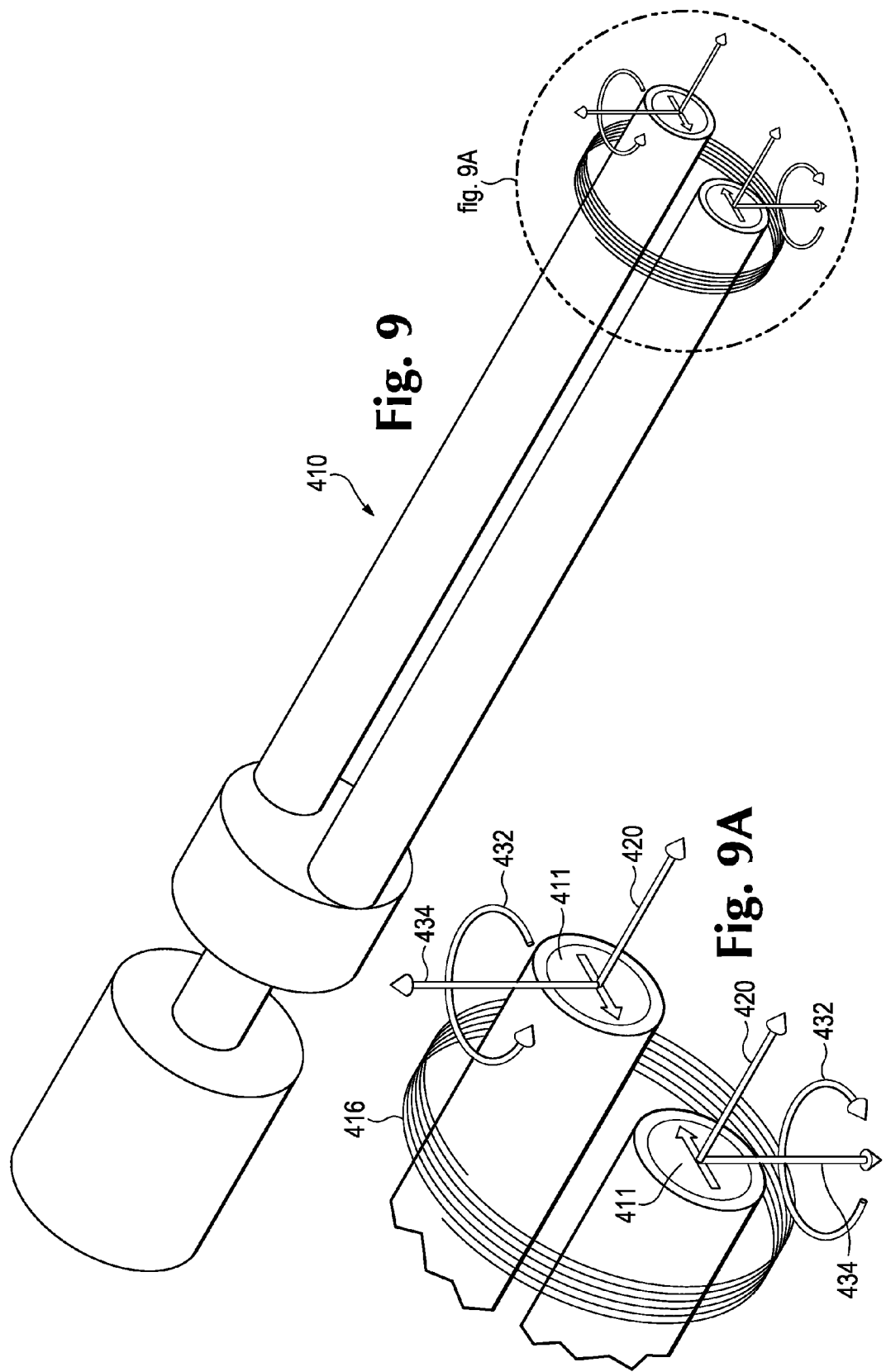

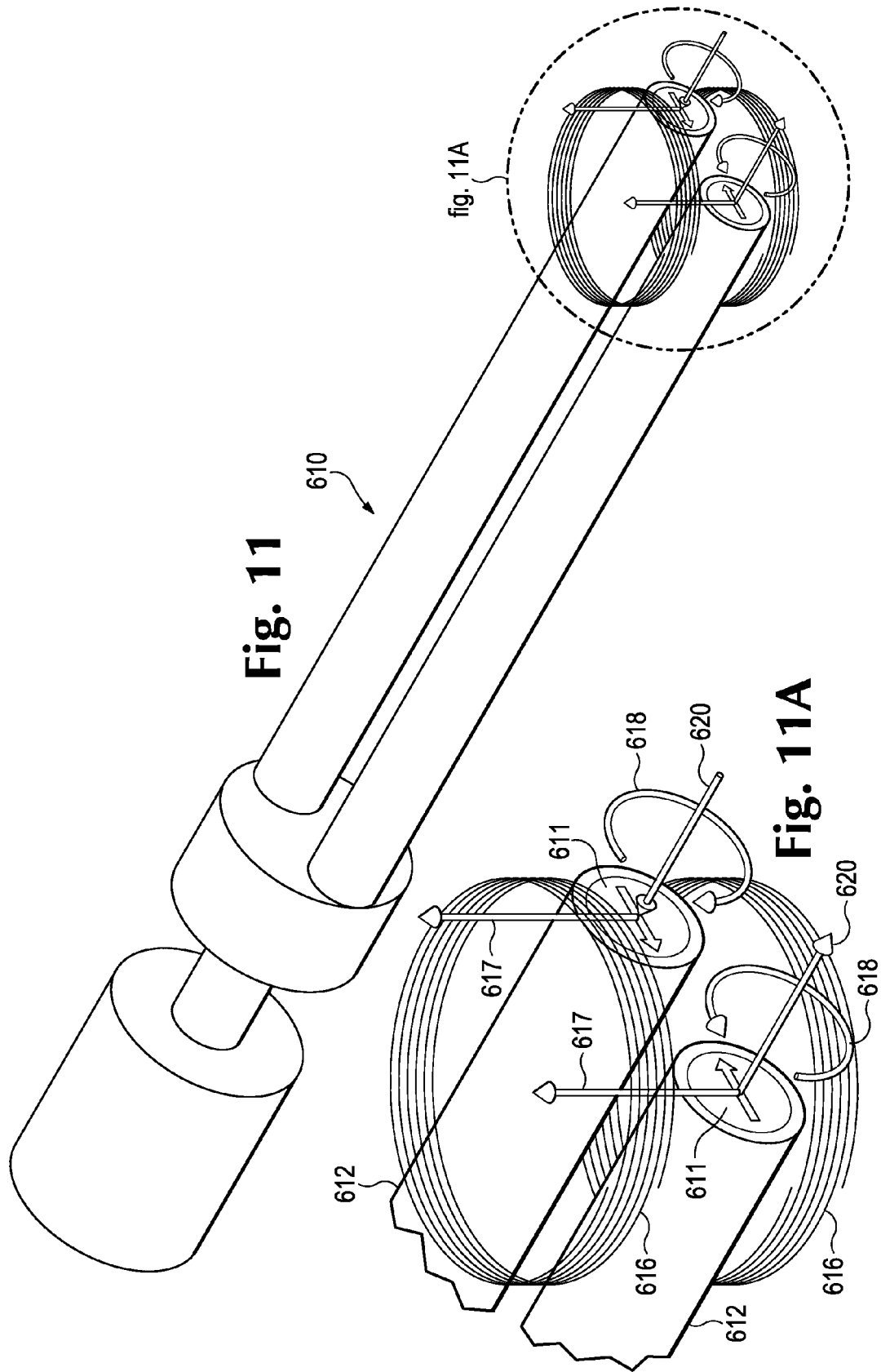

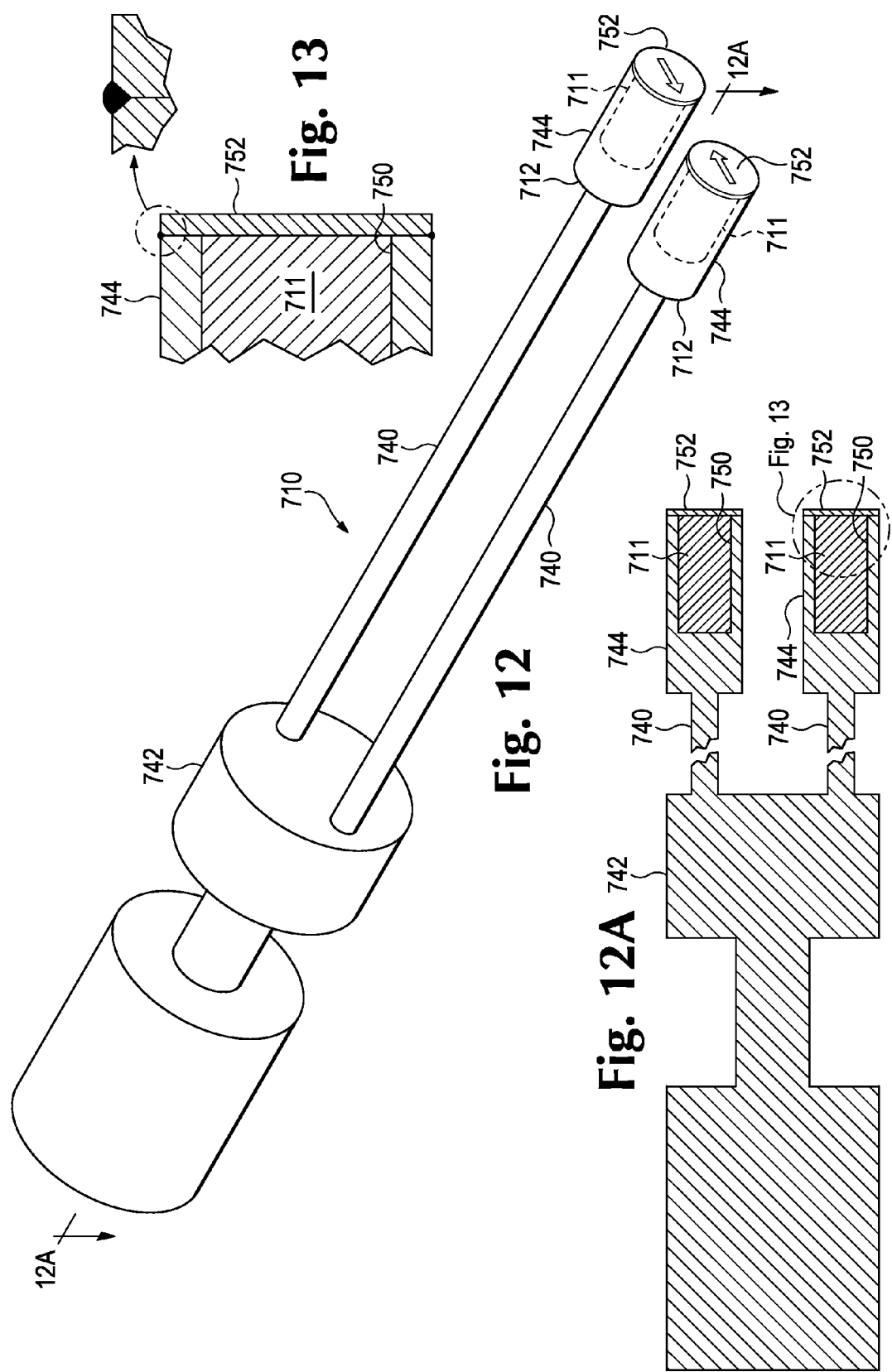

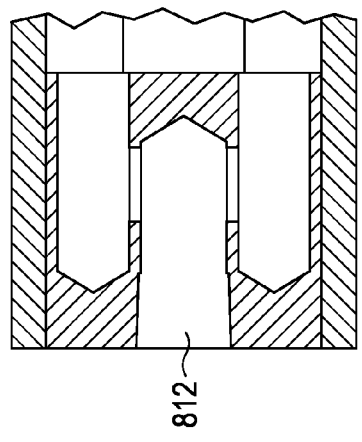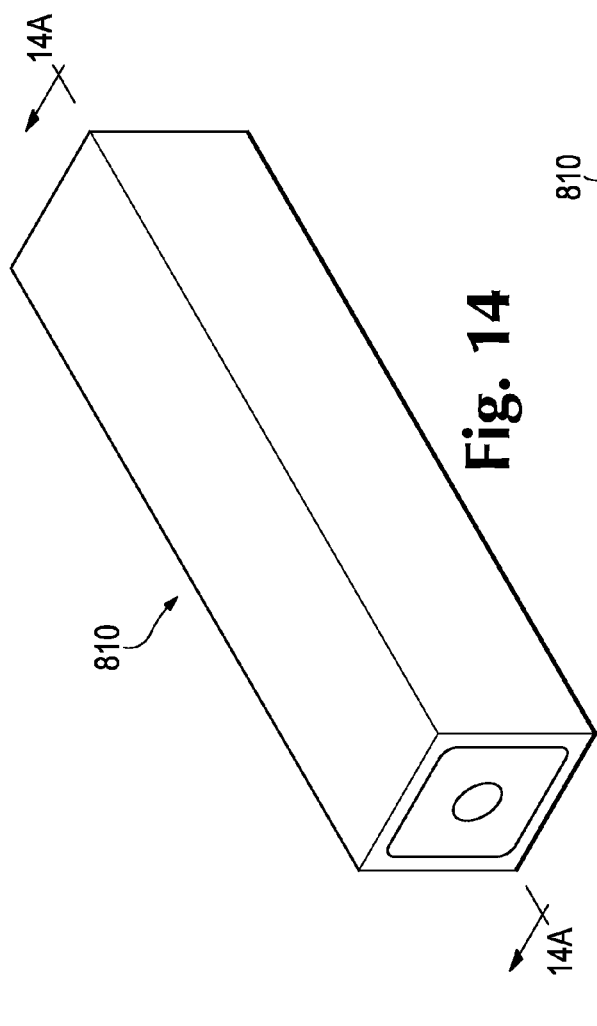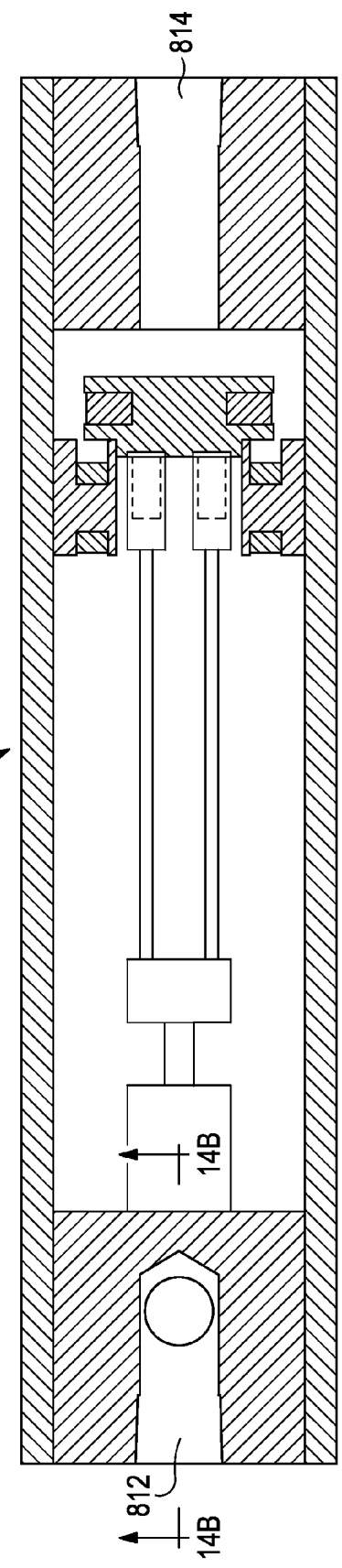

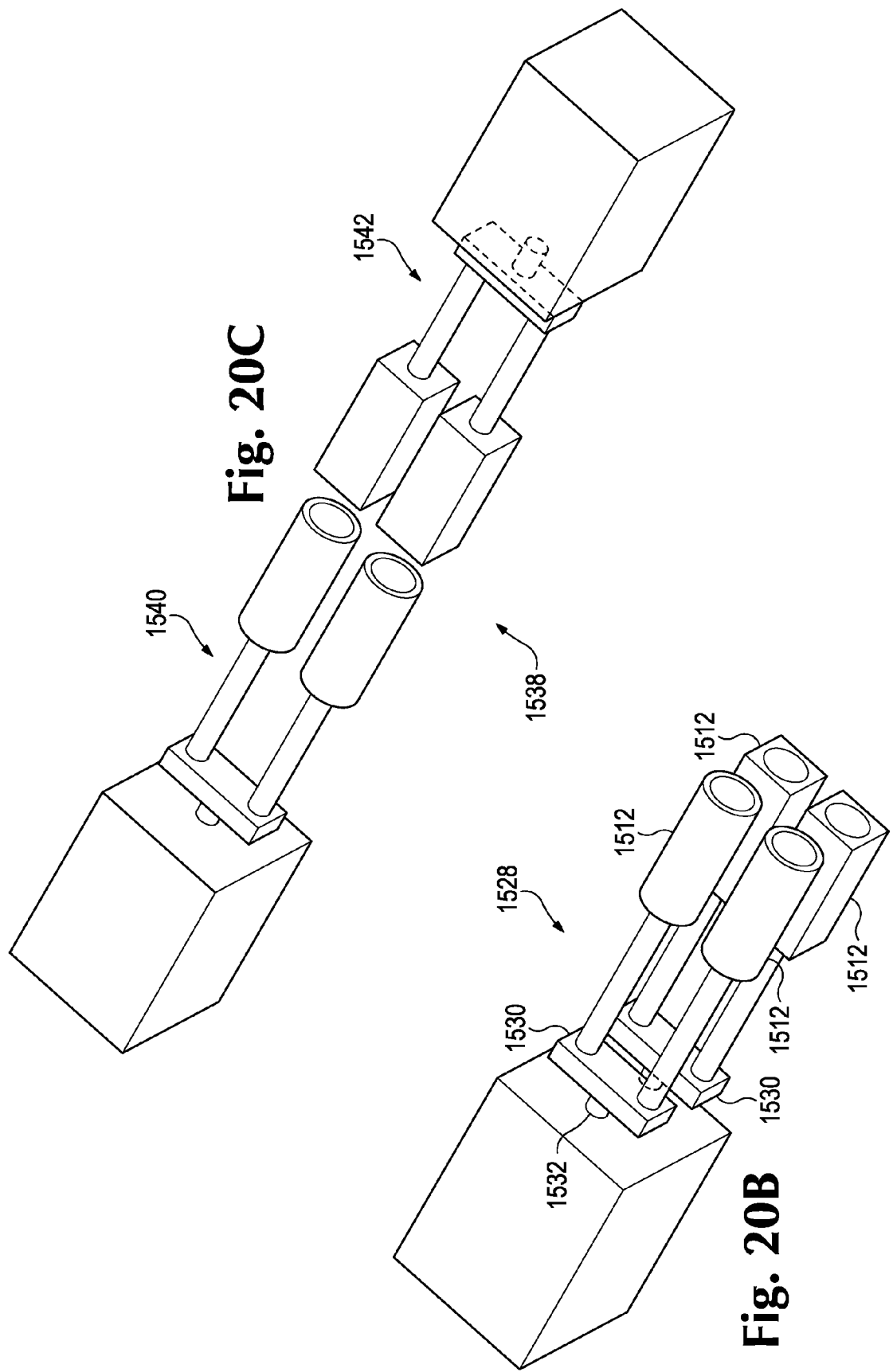

COUPLED TORSIONAL RESONATORS VISCOMETER

BACKGROUND

Resonators find many applications, one of which is the measurement of fluid properties. In some environments, such as in an instrument package mounted in close proximity to an oil or gas well-drilling tool, viscometers are subjected to large and variable forces exerted on the structure by which the resonator is mounted in its casing. These forces have the potential to affect the accuracy and/or reproducibility of the measured fluid properties. A further feature of the oil drilling environment is extremely high pressures, which have the potential to distort or collapse any structure that surrounds a void. This requires that any void in a measurement device, have a passage for fluid entry, to balance the force on the walls defining the void, or else be surrounded by a robust pressure vessel.

Separately, tuning forks are frequently employed as resonators used to measure fluid properties. A conventional tuning fork 10, an example of which is shown in FIG. 1, consists of two tines 12, typically of flat or circular cross section, that are attached to a cross beam 14, which is attached to a mounting base structure 16. The cross beam is frequently integrated with the two tines so as to resemble a single U shaped element. If such a tuning fork is excited at its resonant frequency and immersed in a fluid, it will both move fluid through the transverse motion of its tines, and shear the fluid at the surface that is parallel to the motion of the tines. The resonant frequency of the vibration due to the motion of the tine surfaces that are perpendicular to the direction of tine motion will be most strongly affected by the density of the fluid these surfaces push against. But the damping of the vibration due to the motion of the tine surfaces that are parallel to the direction of tine motion will be most strongly affected by the viscosity of the fluid being sheared by these surfaces.

BRIEF DESCRIPTION OF THE DRAWINGS

FIG. 7 is a perspective view of an additional preferred embodiment, according to the present invention.

FIG. 8 is a perspective view of a magnetic assembly, adapted to be utilized as an element of preferred embodiments.

FIG. 9A is a perspective view of a resonator assembly according to the present invention, utilizing the assembly of FIG. 8.

FIG. 9B is a detail of the resonator assembly of FIG. 9A, taken along circle 9A.

FIG. 11 is a perspective view of a preferred embodiment of a resonator assembly, utilizing the assembly of FIG. 10.

FIG. 12 is a perspective view of a further preferred embodiment of a resonator according to the present invention.

FIG. 12A is a longitudinal section view of the embodiment of FIG. 12, taken along line 12A-12A of FIG. 12.

FIG. 13 is an enlarged detail view of the section view of FIG. 12A, showing the area indicated by circle B, in FIG. 13.

FIG. 14 is a perspective view of a resonator assembly, according to the present invention.

FIG. 14A is a longitudinal section view of the resonator of FIG. 14, taken along line 14A-14A in FIG. 14.

FIG. 14B is a cross-section view of the resonator of FIG. 14A, taken along line 14B-14B of FIG. 14A.

FIG. 20B is a perspective view of an alternative embodiment of the resonator of the assembly of FIG. 20A.

FIG. 20C is a perspective view of an alternative embodiment of resonator assembly.

DETAILED DESCRIPTION OF THE PREFERRED EMBODIMENTS

Definitions, for this application:

Flexure, for a longitudinal element, is used to refer to flexure or bending along the longitudinal axis.

Torsion, for a longitudinal element, is used to refer to twisting about the longitudinal axis.

Coil, is used to refer to an electromagnetic coil, typically comprising a wire coiled about a core of magnetizable material, such as iron, or without such a magnetizable core.

Compliance is the ease with which an object deforms in response to an applied force, the more compliant the less force is needed to cause deformation.

The term "set" includes a single element set.

DISCLOSURE

Figure 1:
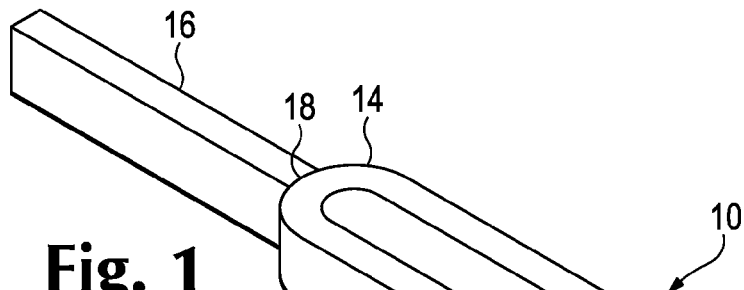
FIG. 1 is a perspective view of a standard tuning fork resonator.
Figure 2:
FIG. 2 is a perspective view of the tuning fork of FIG. 1, vibrating in its first symmetrical bending mode.

In a preferred embodiment, a fluid properties measurement device uses two vibrational modes, a translational mode, which is more sensitive to density of the fluid in which it is immersed and a torsional or rotational mode, which is more sensitive to viscosity. FIG. 2 shows the conventional tuning fork 10 vibrating in its first symmetrical or balanced bending mode, in which a set of two tines 12, joined by a crossbeam 14, affixed to a base structure 16, move in opposite directions in the plane of the fork 10, with a single nodal point 18 at the point of attachment of the crossbeam 14 to the base structure 16.

Figure 3:
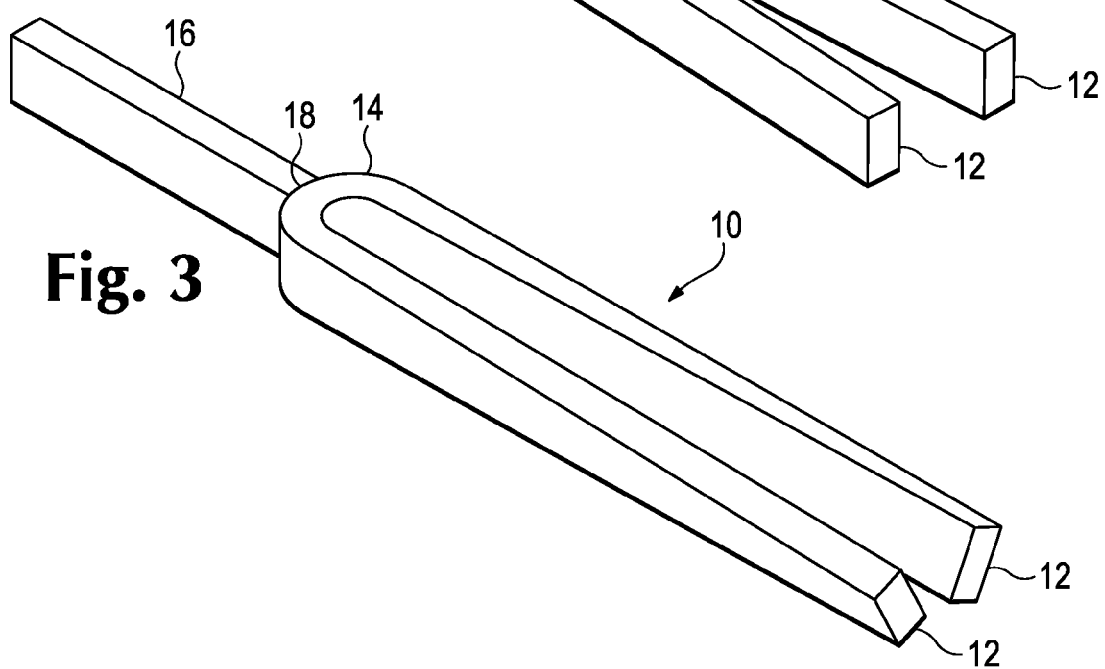
FIG. 3 is a perspective view of the tuning fork of FIG. 1, with its tines vibrating their first symmetrical torsional mode

FIG. 3 shows the same tuning fork 10 with its tines 12 vibrating in its first symmetrical or balanced torsional mode, wherein the tines 12 are twisted in opposite directions about their longitudinal axes.

If, as for resonator 10, the tines are flat, the torsional vibration of the tines will result in displacement of fluid perpendicular to the surfaces of the tines, resulting in a substantial effect of density on the frequency of the torsional mode.

Figure 4:
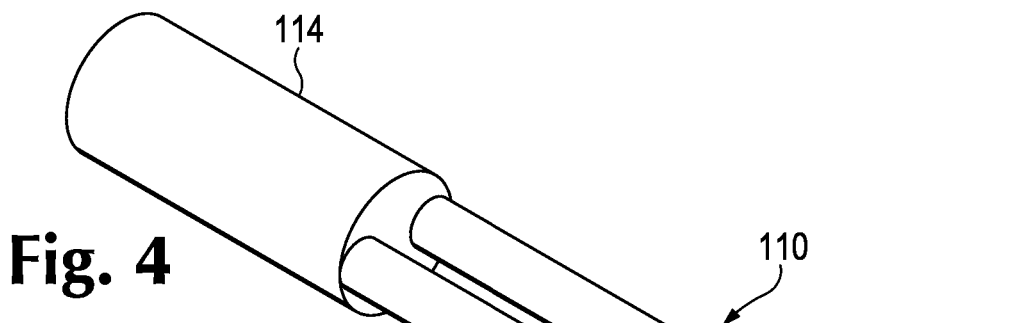
FIG. 4 is a perspective view of a preferred embodiment of a tuning fork according to the present invention.

Referring to FIG. 4, a first preferred resonator embodiment 110 has tines 112, attached to a base structure 114, that are circular in cross-section. Consequently, torsional vibration of the tines 112 will result in predominantly shearing movement of the fluid, with mass movement confined to a thin boundary layer surrounding the tines 112. Because the tines 112 will shear the fluid, the tuning fork in this torsional mode will experience a mechanical damping that depends strongly on the viscosity of the fluid. And similarly to the tuning fork with flat tines, transverse bending of the tines 112 will displace fluid perpendicular to the direction of motion, resulting in mass loading of the resonator, which will strongly influence its resonant frequency.

Resonator 110 still suffers from mounting effects on its frequency and damping measurement. Although the tuning fork's 110 forces are balanced in a direction perpendicular to its longitudinal axis, the mass of the tines is displaced slightly along the longitudinal axis, leading to small longitudinal forces in the base structure 114, which can result in some energy leakage into the mounting, resulting in errors in the damping measurement.

Figure 5:
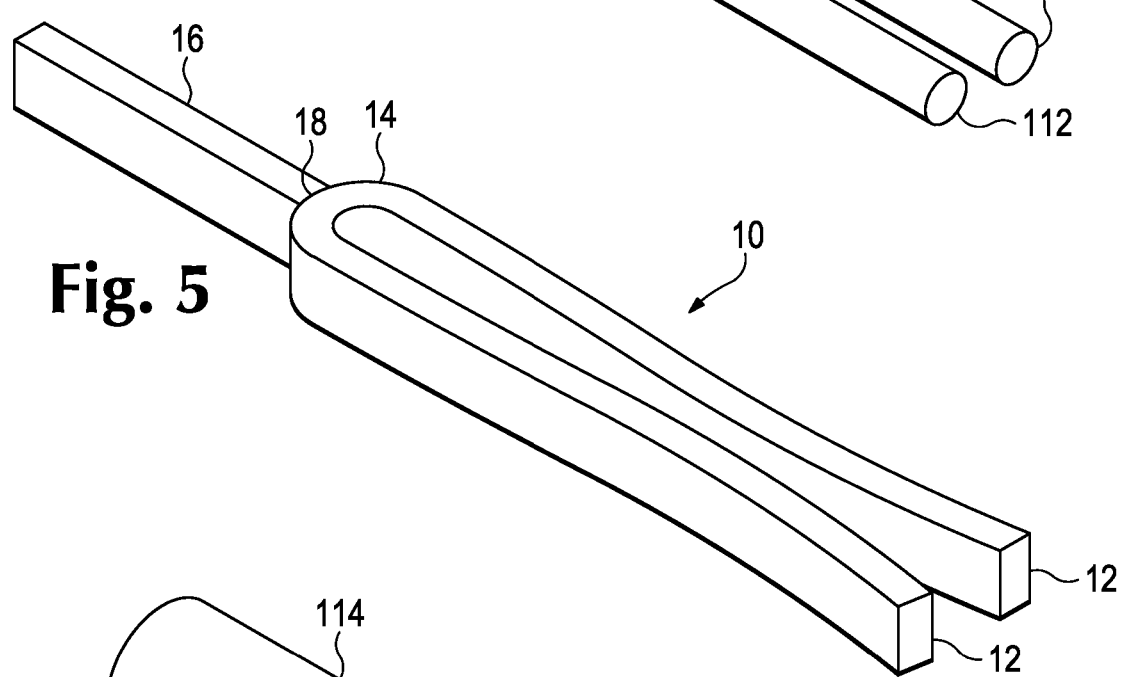
FIG. 5 is a perspective view of the tuning fork of FIG. 1, vibrating in its second bending mode.
Figure 6:
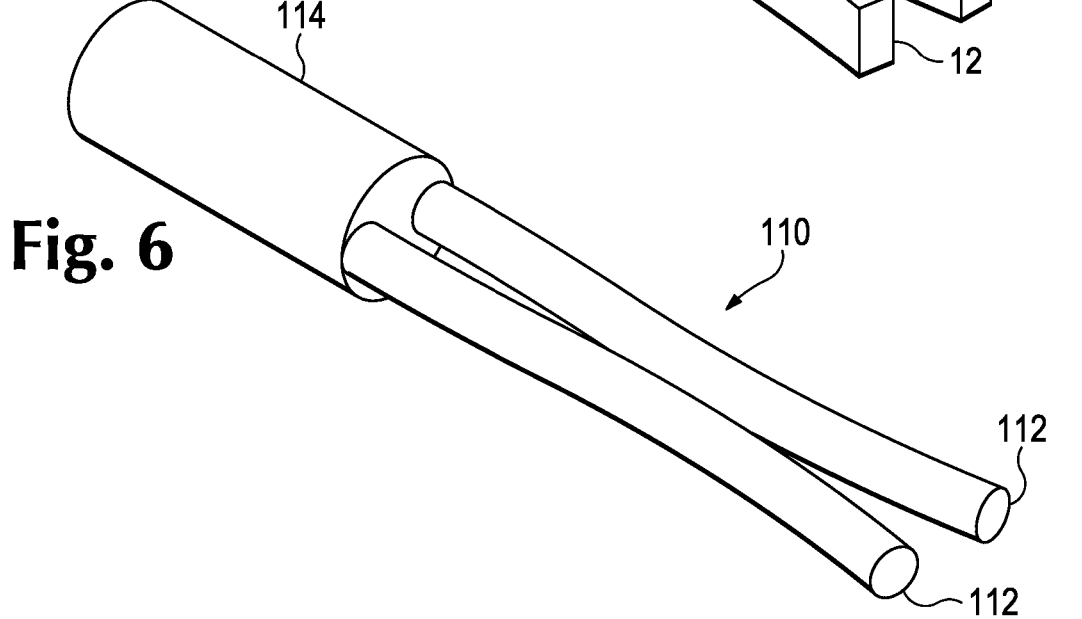
FIG. 6 is a perspective view of the tuning fork of FIG. 4, vibrating in its second bending mode.

Referring to FIG. 5, conventional tuning fork 10 is shown, but this time with the tines 12 vibrating in the second bending mode, in which there is a nodal point 20 on each of the tines at some point between its anchored and free ends. The vibrational forces of the vibrating free ends are largely counterbalanced by the antinodes between the anchored end and the nodal point, resulting in a substantially smaller force on the base structure 16, thereby greatly reducing the effects of mounting conditions on the frequency and damping of the resonator 10. FIG. 6 shows resonator 110 vibrating in a second symmetric bending mode, having a nodal point 120 on each of tines 112.

Operating a tuning fork in the second bending mode has the added benefit that this second mode has a resonant frequency that is much higher than the first transverse resonant frequency, typically, for tines of uniform characteristics, approximately six times that of the fundamental transverse mode. This higher frequency can be an important benefit when the instrument must be operated in an environment that transmits strong ambient vibration to it. Having a means to raise the resonant frequency allows moving that resonant frequency to a range that is typically substantially higher than the highest ambient vibrational frequencies, thereby effectively isolating the resonator from ambient vibrational effects.

Referring to FIG. 7, in a further preferred resonator embodiment 210, having a set of two tines 212 and a base stem 214, tines 212 are directly connected to a base bridge 220, which in turn is connected to base stem 214 by a neck 216, which has a substantially reduced thickness, and therefore reduced torsional and bending stiffness, thereby having increased compliance, and thereby reducing the mechanical energy coupled out of the tuning fork into the mounting through the base 214. In further embodiments, neck 216 is made of a more compliant material, or is hollow, or has a complex cross-sectional shape, and therefore more compliant than base stem 214. Embodiment 210 is considered to have a base structure that includes base stem 214, base neck 216 and base bridge 220.

Any applicable means may be used to excite and measure the resonant characteristics of the tuning fork, such as piezoelectric elements, or electromagnetic means. Referring to FIG. 8, a cylindrical magnet and coil assembly 310 is shown, having a magnet 311 that is diametrically polarized. That is, its magnetic polarization vector 312 is perpendicular to its cylinder axis 314. When magnet 311 is immersed in a magnetic field parallel to its cylinder axis 314, which has been generated by a solenoid coil 318 that is coaxial with the magnets cylinder axis 314, the axial field generated by the coil interacts with the magnetic field of the magnet so as to produce a torque 320 about an axis 322 mutually perpendicular to the applied field 316 and the magnets direction of polarization 312. Also, rotating the magnet about an axis coincident with the torque vector 322 induces a voltage in the coil 318.

Referring to FIG. 9, in one preferred resonator embodiment 410, otherwise the same as the resonator 210, magnets 411 are embedded in a set of two cylindrical tines 412. Additionally, a coil 416 is positioned coaxially with respect to the magnet 411.

Furthermore, in resonator 410, the magnetic polarization vectors of magnets 411 in the two tines 412 oppose one another, so that the two north poles face one another, and the two south poles face away from each other. The coil 416 is used to create a magnetic field having a direction vector coaxial with the longitudinal axes 420 of the two tines 412. This causes for both of the tines 412, a torque 432 about an axis 434 perpendicular to the plane containing the two tines, and going through the geometric center of the magnet 411.

This results in the two tines 412 experiencing equal but opposite torques, which results in the tines 412 being bent in the plane containing them, and in opposite directions, since the magnetic axes 420 of the magnets 411 in the two tines 412 oppose one another. The axial coil 416 can be used to excite either the first or the second transverse bending mode of the resonator 410, depending on the frequency with which it is excited. Similarly, because the motion of the tines 412 induces a voltage in the coil 416, it can be used to monitor the vibrational amplitude and phase of the resonator if it is connected to an amplifier and an indicating instrument. By first exciting the tuning fork to resonance, switching off the excitation, and then measuring the decay, fluid property measurements can be performed.

Figure 10:
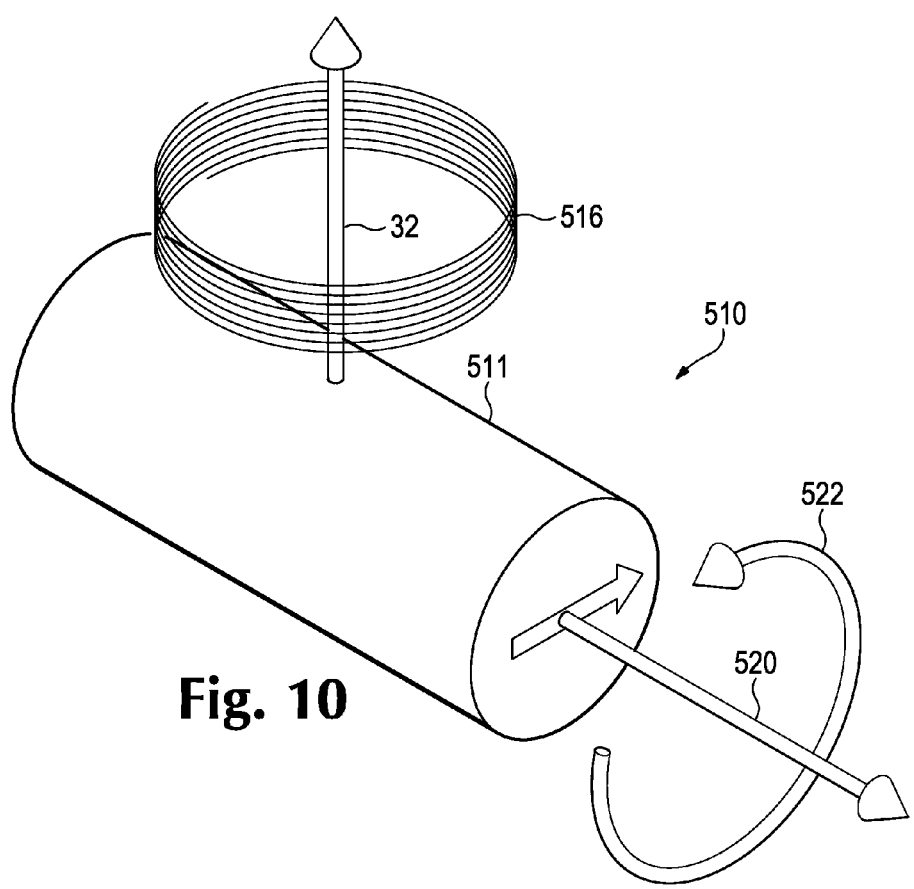
FIG. 10 is a perspective view of an alternative embodiment of a magnetic assembly, adapted to be utilized as an element of alternative preferred embodiments.

Referring to FIG. 10, a magnet and coil assembly 510 is shown, which is similar to assembly embodiment 310, but having a coil 516 with an axis that is perpendicular to a plane containing the cylinder axis 520 of a magnet 511, which coincides with the polarization direction of the magnet 511. Accordingly, a current flowing through the coil produces a torque 522 on the magnet parallel to its cylinder axis 520. Conversely, a rotation of the magnet about its cylinder axis induces a voltage in the coil 516.

FIG. 11 shows a resonator embodiment 610, utilizing the magnet and coil assembly 510, and in which magnets 611 are set into the ends of a pair of tines 612, a current through a pair of coils 616, which is positioned so that its magnetic axis 617 is perpendicular to the plane containing the tines 612. For each tine 612, this produces a torque 618, about a torque vector 620 on the tine 612 parallel to its longitudinal axis 620. Because the magnetic vectors of the two magnets 611 are opposed, as in resonator 410, the torques 618 are in opposite rotational directions, similarly twisting tines 612 in opposite directions. When the tines 612 oscillate in torsion, they induce voltages in the two sensing coils 616 proportional to their angular velocity, enabling measurement of the amplitude and phase of their torsional oscillation.

In FIGS. 12 and 12A, an alternative configuration of a tuning fork resonator 710 is shown in which the tines 712 are not of uniform cross section, but consist of thin rods ("tine stems") 740 connected to the decoupling disk 742, and terminated in short rods 744 of larger diameter, which serve as holders for the magnets 711. Because the torsional stiffness of a uniform rod is proportional to the fourth power of its radius, the majority of the twist of the resonator occurs in the thin rods, while the thick terminal rod sections function as substantially rigid torsional inertial masses. The resonator 710 functions as a lumped-constant resonator, whose frequency is determined by the torsional spring constant of the tyne stems 740 and the torsional inertia of the thicker terminal rods 744. In the case of bending vibrations, the moment of rotational inertia of the cross section about the neutral axis of bending has a strong effect on the speed of bending waves, thus permitting a resonator designer to pick the resonant frequencies by picking the structural characteristics of the tines 712. One advantage of embodiment 710 is that it is possible, by making the tine stems 740 sufficiently compliant and the terminal rods 744 sufficiently massive, to set the torsional resonant frequencies substantially lower than they would be in the embodiments 210, 310, thereby giving the resonator designer greater flexibility in designing a sensor that has a desired torsional resonant frequency, even with dimensions constricted by its application. Moreover, construction details of the resonator 710 may be tailored to environmental conditions of an intended use, such as the high pressure encountered in downhole applications. For example, constant dimension tines tend to have void spaces that can be eliminated in resonator 710.

FIG. 13 shows the details of the magnet mounting in the sensor. The magnet holders 750, whether they are simply the ends of a uniform-bar distributed mode resonator, or they are incorporated into the terminal rods in the case of a lumped-mode sensor, are bored out to a diameter slightly smaller than the diameter of the magnets 711 they will contain. The magnets 711 are then pressed into the rod ends in such a way that they contact the bottom of the hole, and are flush with the end of the rod. A cap 752 is then welded over the end of the rod, forming a hermetically sealed, void-free container for the magnet. The magnet is protected from possibly aggressive media in which the resonator is immersed, and the freedom from voids insures the structural integrity of the magnet assembly under the highest operating pressures.

FIGS. 14, 14A and 14B detail a possible configuration of a completed sensor assembly 810, although many more variations are possible. Assembly 810 is a completely self-contained unit which can be connected to a fluid-flow system using inflow tube 812 and outlet tube 814. In practice, for high pressure applications, the entire system would be immersed in a fluid with the same pressure and temperature as the fluid whose characteristics are to be measured. The inflow tube 812 and the outlet tube 814 enable a representative sample of the fluid to be pumped through the sensor unit, ensuring turnover of the fluid by preventing formation of stagnant pockets.

Figure 15:
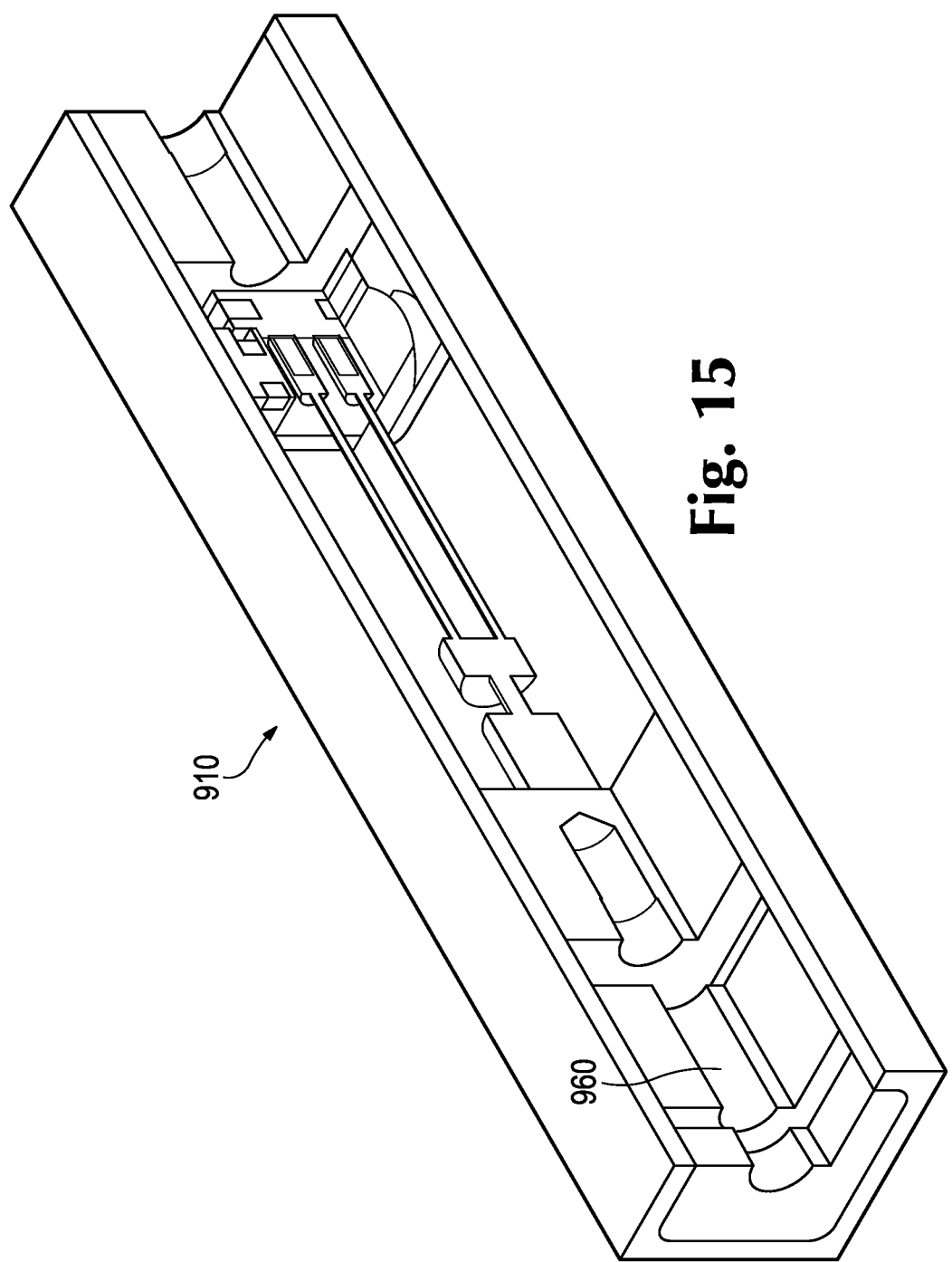
FIG. 15 is a perspective cut-away view of an alternative preferred embodiment of a resonator assembly.

A possible limitation on the functioning of the sensor assembly 810 can occur when the fluid to be measured contains suspended magnetic particles, which could adhere to the surface of the sensor in the neighborhood of the magnets embedded in the sensor, changing its configuration and therefore altering its resonant properties. FIG. 15 shows a sensor assembly embodiment 910 that addresses this drawback, by adding a magnetic particle trap 960 added to the inflow tube just before the sensor unit proper.

The magnetic particle trap 960, consisting, for instance, of a magnetic plug, or of two or more permanent magnets forming a slot or annulus through which the fluid must flow, is of a type known to skilled persons and is a common feature of other fluid flow systems in which it is desired to prevent magnetic particles from entering a system whose operation they could disturb. Assembly 910, among a variety of other possible configurations, fulfills the requirement of a compact, robust viscometer-densitometer instrument that is capable of accurate measurement in a severe environment, typical of measurement-while-drilling applications, that includes high pressure, high temperature, high ambient vibration levels, and large and variable forces exerted on the housing in which the resonator is mounted.

Calculation of Damping

Figure 16:
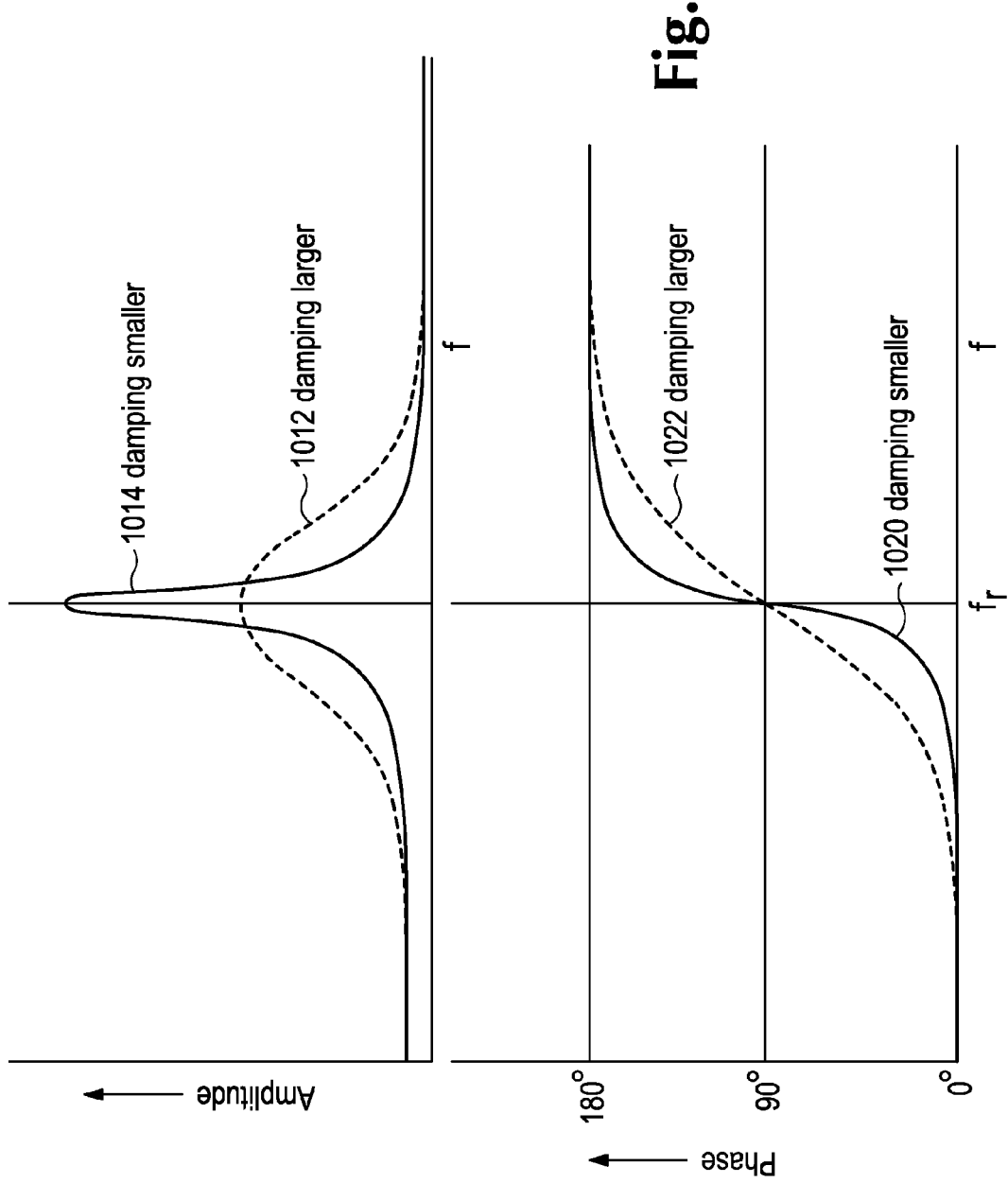
FIG. 16 is a graph showing magnitude and phase shift, parametric in frequency, about a resonant frequency, for two liquids having different viscosities.

FIG. 16 shows the magnitude (top graph) and phase shift (bottom graph) response of a resonator to a sinusoidal driving signal. Curve 1012 is the amplitude response of the resonator in a high damping environment, whereas curve 1014 shows the response in a low damping environment.

There are numerous approaches to using these characteristics to measure fluid properties, many of which are well known from the literature. Two of these approaches involve sweeping through a range of frequencies in the vicinity of the resonance, and either measuring the ratio of the oscillation amplitude to the excitation amplitude or finding the peak of the resonance amplitude curve, which corresponds closely with the resonant frequency. The damping factor can be computed from the ratio of the amplitude of the resonator to the amplitude of excitation at the resonant frequency fr.

Furthermore, the more highly damped the resonator, the broader will be the peak of the resonance curve. The frequency difference between two fixed points, such as the 1/e points or the ½ peak amplitude points, is a measure for the damping of the resonator. The resonator may be excited at its resonant frequency, and the excitation switched off, resulting in a decaying vibrational amplitude. The characteristic decay time of the amplitude is a measure for the damping of the resonator.

Figure 17:
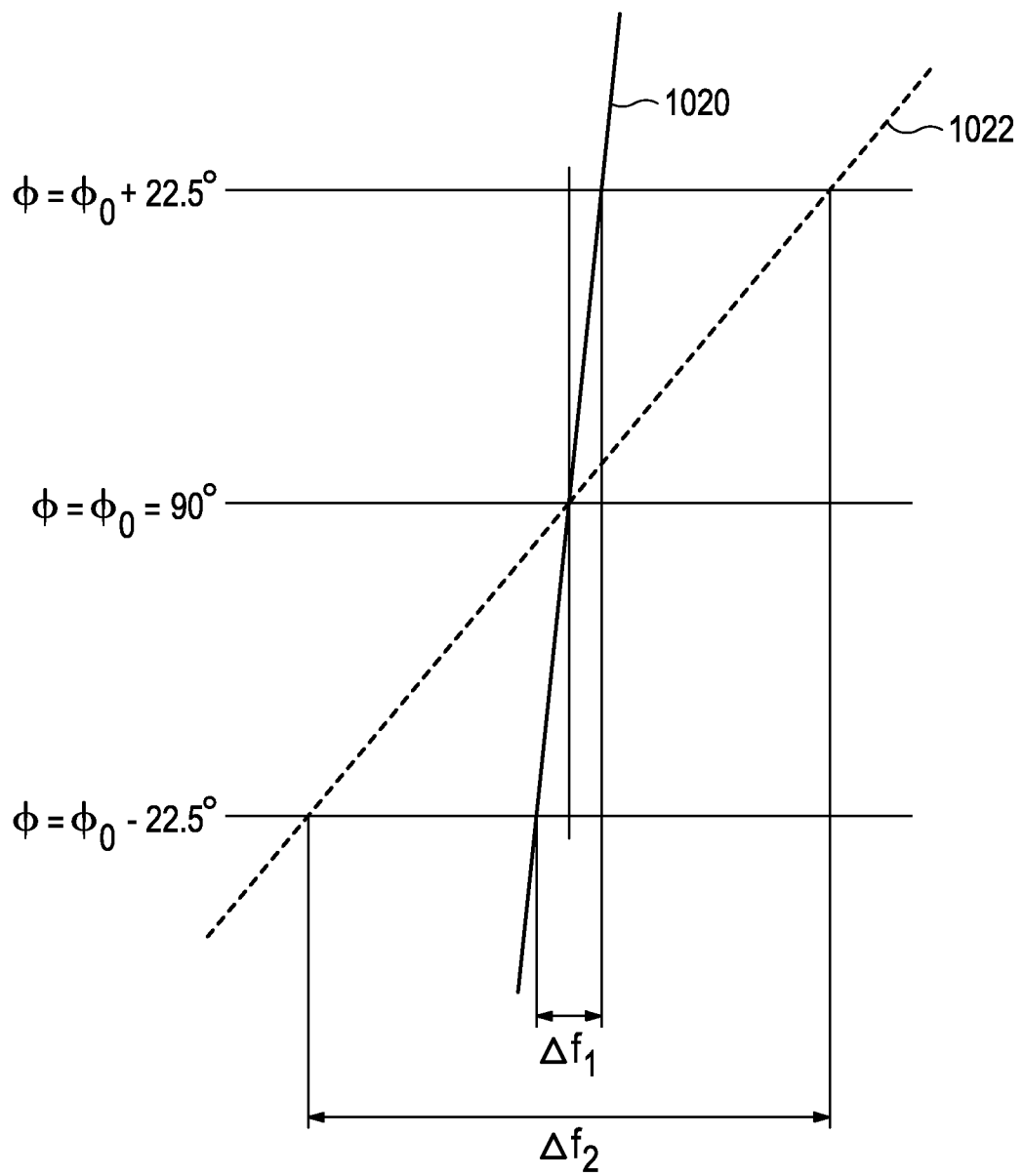
FIG. 17 is a graph showing phase shift, parametric in frequency, for the two liquids of FIG. 16, expanded about the resonant frequency.

FIG. 16, also shows the phase shift in a low damping environment 1020 and high damping environment 1022. The less the resonator is damped, the more rapidly the phase changes as the frequency is swept through the resonant range. FIG. 17 shows phase curves 1020 and 1022 in the immediate vicinity of the resonant frequency. If the excitation frequency is set so as to give a predetermined phase relationship between the excitation and the response, and then to give a second predetermined phase relationship between excitation and response, the difference between those two frequencies is a measure for the mechanical damping of the resonator.

In the method illustrated in FIG. 17, the measurement formed is independent of the amplitude of the vibrations of the resonator. This can be advantageous because it renders the measurement immune from errors introduced by factors such as the strength of the magnetic field of the magnets, the exact number of windings in the coils, the length of the conductors connecting the coils to the measurement electronics, and similar factors. Also, particularly in the presence of interference from electrical and ambient vibrational noise, frequency measurements can be made much more accurately than can amplitude measurements, enabling greater stability and reproducibility of the measurement results. Methods for implementing this phase shift measurement principle are taught by U.S. Pat. No. 5,837,885, which is incorporated by reference as if fully set forth herein.

Figure 18A:
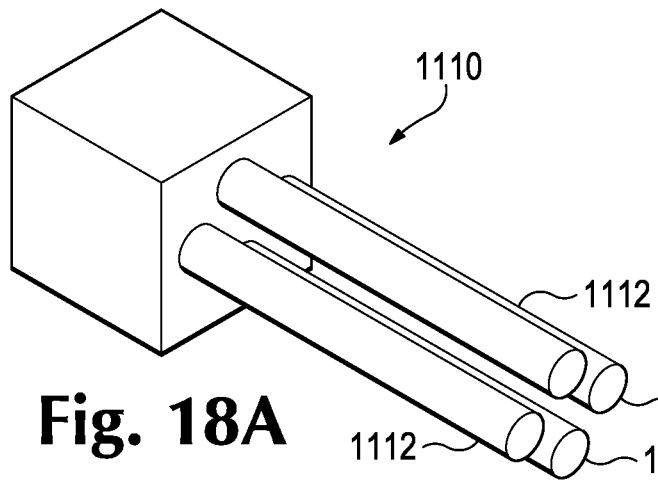
FIG. 18A shows a further alternative embodiment of a resonator, according to the present invention.
Figure 18B:
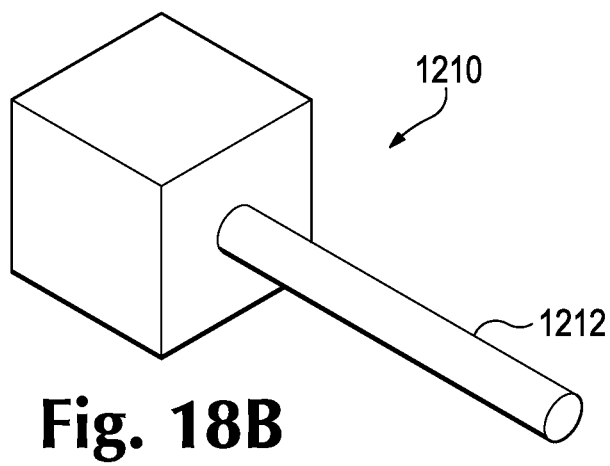
FIG. 18B shows a further alternative embodiment of a resonator, according to the present invention.
Figure 18C:
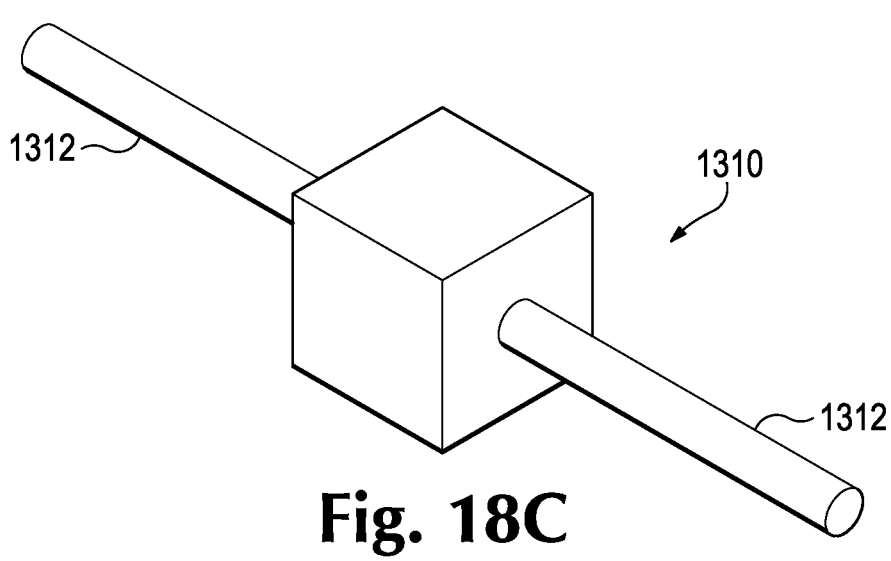
FIG. 18C shows a further alternative embodiment of a resonator, according to the present invention.

FIG. 18A shows alternative preferred resonator embodiment 1110, having four tines 1112. FIG. 18B shows alternative preferred resonator embodiment 1210 having a single longitudinal resonating element 1212. Finally, FIG. 18C shows yet another alternative preferred resonator embodiment 1310, which is a linear arrangement having two opposed longitudinal resonating elements 1312.

Figure 19:
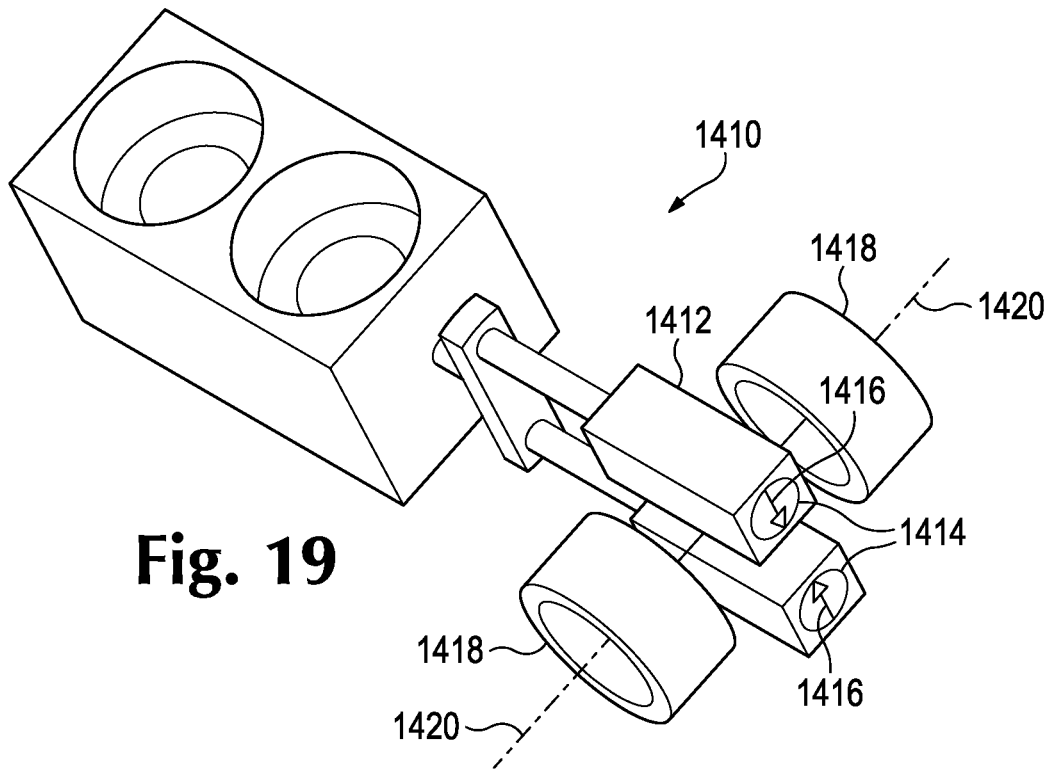
FIG. 19 is a perspective view of a further preferred embodiment of a resonator assembly, according to the present invention.

Referring to FIG. 19, a further preferred resonator embodiment 1410, has tines 1412 that are not circular in cross-section and are excited in torsion to measure the density of the fluid. A tine of circular cross section vibrating in torsion about its cylinder axis moves everywhere tangentially to its own surface, shearing through host fluid. The amount of fluid carried along with the surface is dependent on both the viscosity and density of the fluid, and is contained within the boundary layer characterizing the velocity of the fluid in the neighborhood of the resonator surface. This "apparent mass" is relatively small in the case of circular-tine resonators, resulting in only a small decrease of resonant frequency with increasing density and viscosity.

By contrast, some portions of the surface of non-circular tine 1412 rotating about its own axis move perpendicular to the surface, displacing fluid, and resulting in a greater apparent mass loading than is the case of a cylindrical tine. Therefore, the resonant frequency of resonator 1410 is more strongly lowered by immersion in a dense fluid than is the resonator having tines that are circular in cross-section.

Magnets 1414 in the ends of tines 1412 have opposed polarization vectors 1416. A pair of coils 1418 each produce a magnetic field that has an axis 1420 that is orthogonal to both the longitudinal axes of the tines and the magnetic polarization vectors 1416. An oscillating current flowing through the coils exerts opposite torques on the ends of the two tines 1412, causing them to rotate about their longitudinal axes. This device may be excited in its first torsional mode by means of the coils, which are also used to monitor the motion of the tines by the current created by the tine 1412 movement.

This resonator shows a strong dependence of resonant frequency on the density of the medium in which it is immersed.

Naturally, the tines may be of any cross section in which their motion about their longitudinal axis produces a component of motion normal to the moving surface. Flattened tines, oval or elliptical tines, round-cornered square or rectangular tines are all possible variants.

Figure 20A:
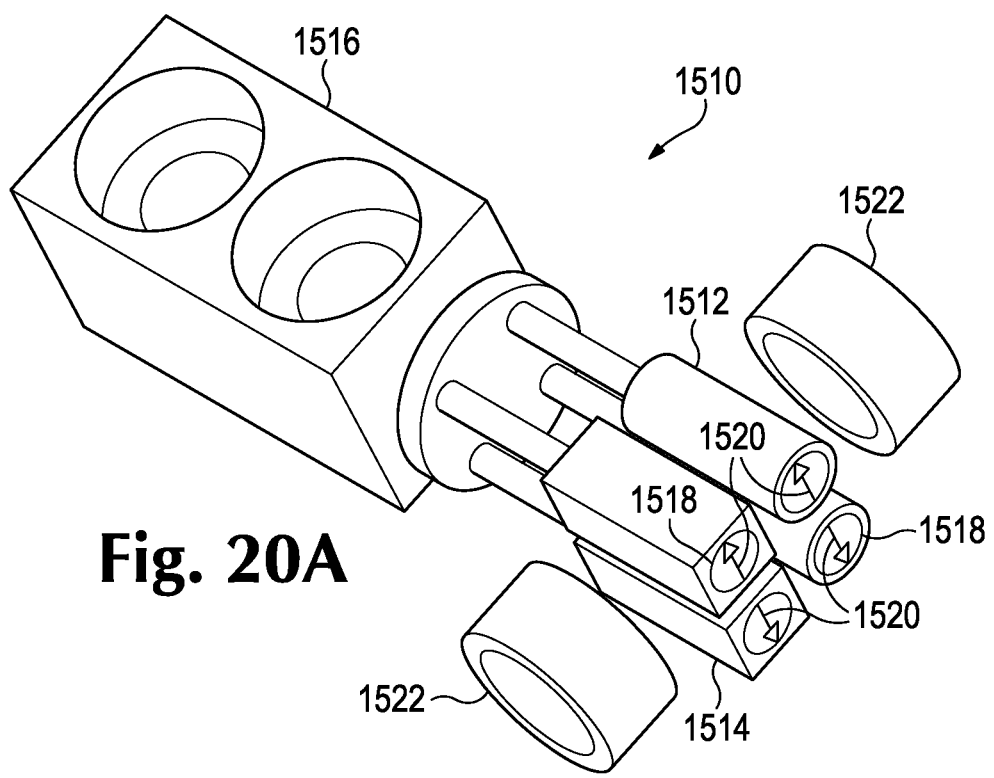
FIG. 20A is a perspective view of a further preferred embodiment of a resonator assembly, according to the present invention.

Referring to FIG. 20A, in another alternative preferred embodiment resonator 1510, a first pair of coupled tines 1512, which are circular in cross-second and a second pair of coupled resonant tines 1514, which are square in cross section. The first pair of tines 1512 and the second pair of tines 1514 are attached to a common mounting 1516. Both tine pair 1512 and tine pair 1514 have magnets 1518 defining polarity vectors 1520 that are mutually opposed. The first set of tines 1512, being circular in cross-section, are primarily sensitive to viscous damping, while the second set of tines 1514 are primarily sensitive to fluid density, with their resonant frequency being shifted in proportion to the resonant frequency.

If the dimensions of first tines 1512 and second tines 1514 are adjusted so that when operating in air, the resonant frequency of tines 1514 are substantially lower than that of the of tines 1512, then a single pair of coils 1522 may be used to independently drive both tines 1512 and tines 1514, allowing sequential measurement of the characteristics of the two pairs of tines 1512 and 1514.

Figure 20D:
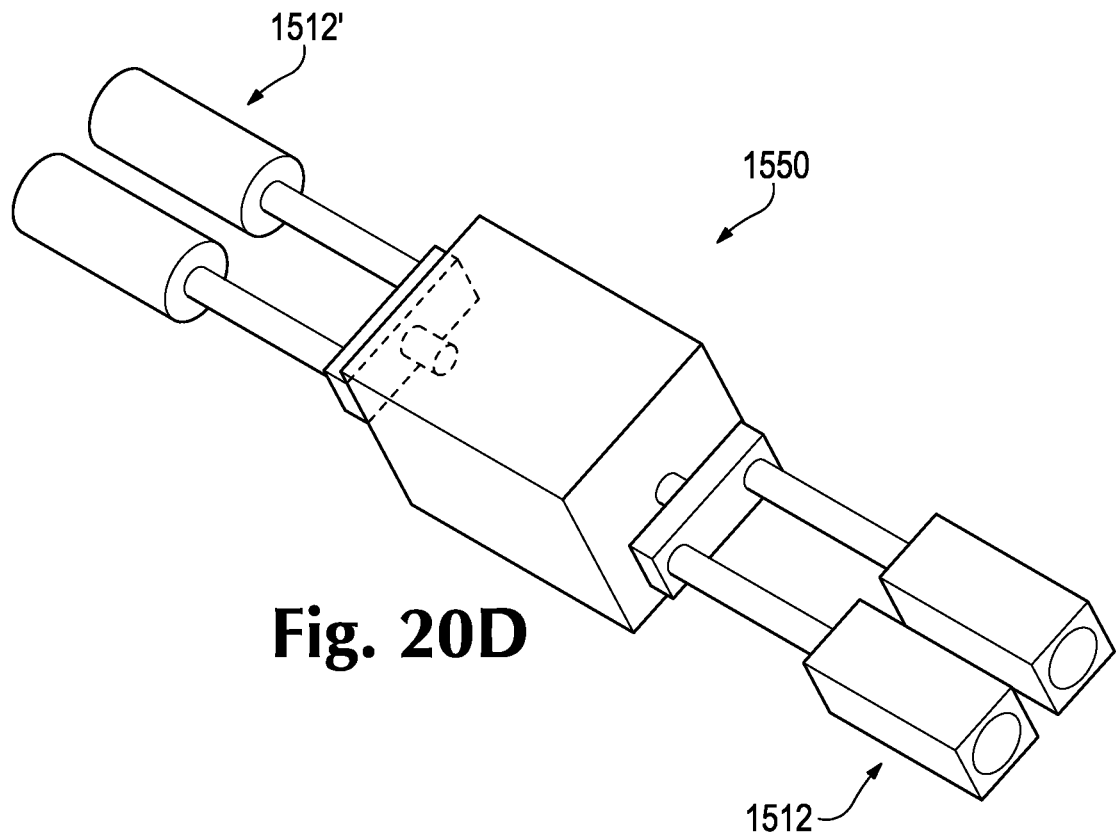
FIG. 20D is a perspective view of an alternative embodiment of a resonator.

Referring to FIG. 20B, refers to an embodiment 1528, wherein movement of tines 1512 can be better isolated by placing tines 1512 on bridges 1530 supported by necks 1532. FIG. 20C shows an embodiment 1538 that more completely isolates tine movement, by having two separate structures, 1540 and 1542, and FIG. 20D shows an embodiment 1550 where two pair of tines 1512 and 1512' extend outwardly in opposite directions. It may be necessary to have two different coil sets in this embodiment, as the tines 1512 and 1512' are so far separated.

Figure 21:
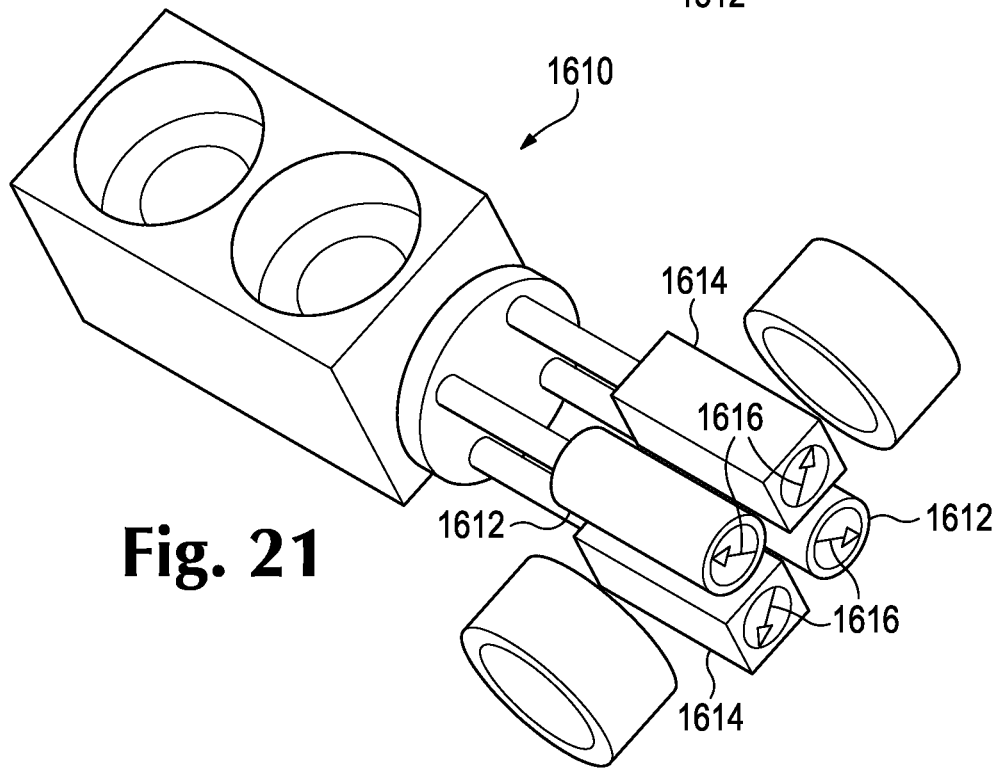
FIG. 21 is a perspective view of a further preferred embodiment of a resonator assembly, according to the present invention.

Referring to FIG. 21, in a further preferred embodiment of a resonator 1610 having a first pair tines 1612 that are circular in cross-section and disposed diagonally from each other and a second pair of tines 1614 that are square in cross-section, and also disposed diagonally, the magnetic polarization 1616 of each horizontally or vertically adjacent pair tines, 1612 and 1614, are all oriented at 90 degrees to one another. This produces a lower net magnetic field at the surface of the tines, making it easier to neutralize for the purpose of freeing the surface of the resonator from unwanted magnetic particles accumulated from the fluid in which the resonator is immersed.

Other variants are conceivable, in which, for instance, the two tuning forks are disposed with tines pointing in opposite directions and sharing a common mounting base structure.

Figure 22:
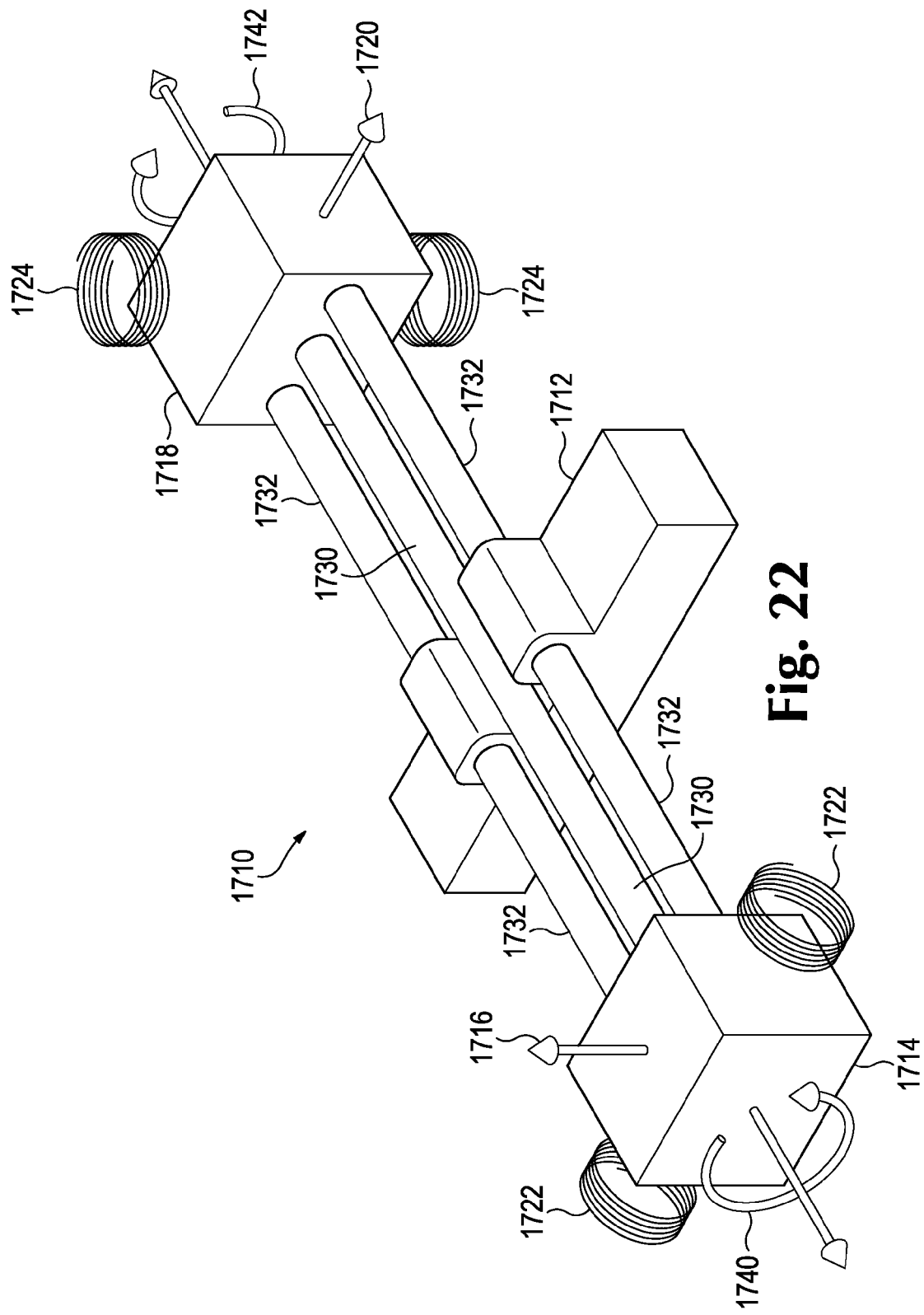
FIG. 22 is a perspective view of a further preferred embodiment of a resonator assembly, according to the present invention.

Referring to FIG. 22 a further preferred embodiment is an axially antisymmetric, non-cylindrical torsional resonator 1710 made up of three sets of rods coupling a nodal support 1712 to a first solid rectangle end mass 1714, having a first magnetic polarization vector 1716 and a second solid rectangle end mass 1718 having a second magnetic polarization vector 1720 that is orthogonal to the first 1716. In this case, the magnetic fields in the two ends are orthogonal to each other. First end mass 1714 is driven by a first pair of coils 1722, and second end mass 1718 is driven by second pair of coils 1724. Coils 1722 and 1724 also measure end mass 1714 and 1718 movement. End masses 1714 and 1718 are joined by a central rod 1730 and a set of four drive rods 1732 that are joined by the nodal support 1712.

The two end masses 1714 and 1718 are driven to rotate in opposite directions 1740 and 1742, respectively. Torsion is produced in the central rod 1730, while a combination of bending and torsion are produced in the torsion springs 1732. The central rod 1730 freely transmits torsional forces between end masses 1714 and 1718. It is only necessary to excite the resonator 1710 at one end (although it could as easily be excited at both ends). Similarly, because of the symmetry of the system, it is only necessary to measure the motion of the resonator 1710 at one end.

It is possible that the fluid whose properties are to be measured may contain magnetic particles. Because preferred embodiments described above have magnets embedded in the ends of their tines, these would be susceptible to accumulation of magnetic particles with time, which could alter both the resonant frequency of the sensor as well as its damping. This could result in erroneous readings.

Figure 23:
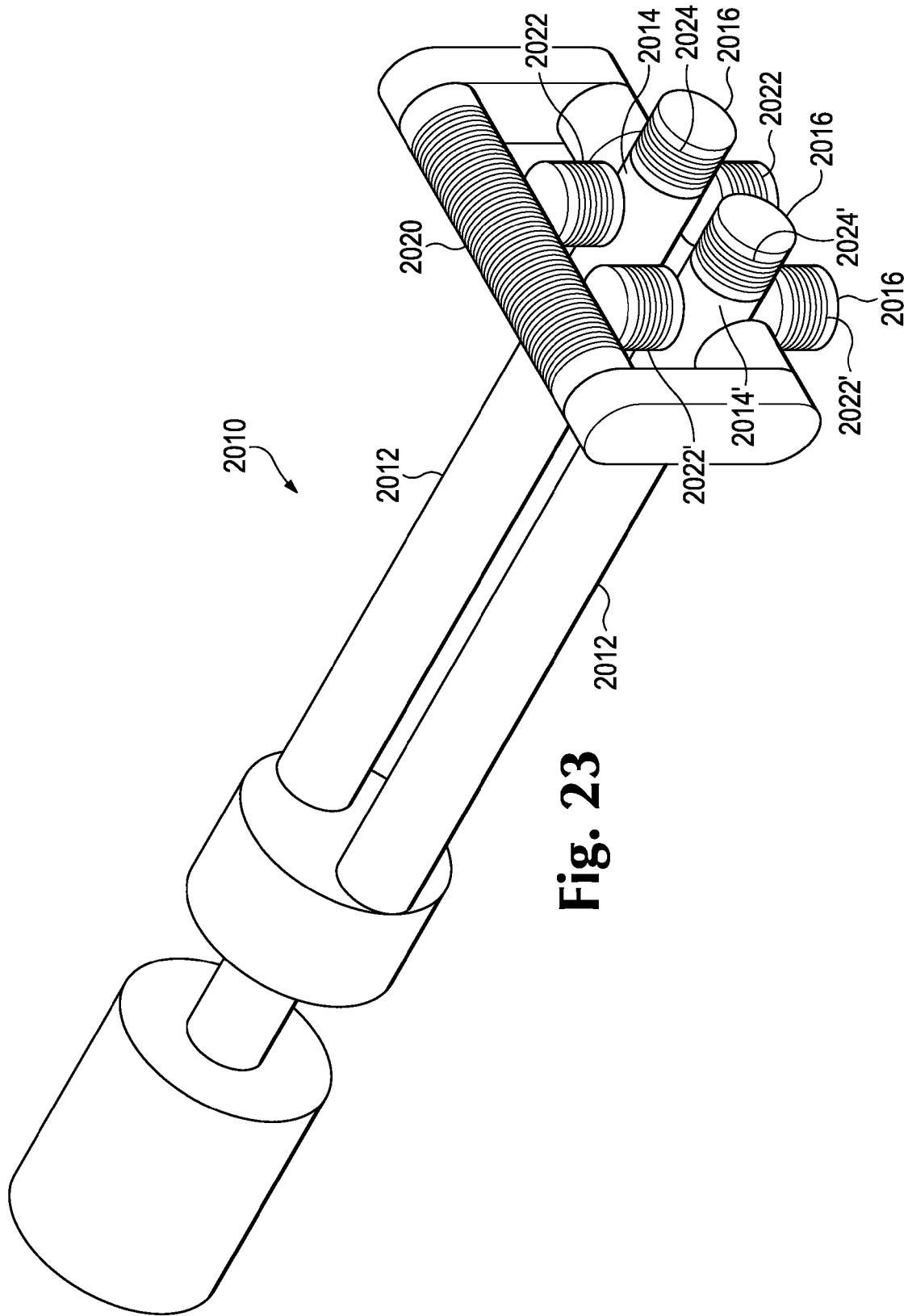
FIG. 23 is a perspective view of a preferred embodiment of a magnetic particle resistant resonator assembly, according to the present invention.

FIG. 23, shows a preferred embodiment of a resonator 2010 having tines 2012 that house magnetic material elements 2014 and 2014'. In one preferred embodiment elements 2014 and 2014' are of a soft ferromagnetic material, such as soft iron, ferrite, or some other magnetizable and de-magnetizable material. Slugs 2014 and 2014' are sealed into the tine ends with a cap 2016, preferably of inconel, and so are protected against corrosion. Slugs 2014 and 2014' are magnetized by being immersed in the field of a strong coil 2020. This permits slugs 2014 and 2014' to function in much the same manner as the permanent magnets in the resonators 410 and 610 etc. In a preferred method, the coil 2020 is periodically switched off, which serves to demagnetize the magnetic slugs, permitting any accumulated magnetic particles to be washed away by the fluid flow through the sensor. Alternatively, the same effect is achieved by driving coil 2020 with an alternating current drive.

In an alternative preferred embodiment, magnetic elements 2014 and 2014' are made of alnico or ferrite ceramic, or some similar high-temperature permanent magnet material, with a lower field strength than the rare earth magnets used in resonators 310, etc. In this case, the resonator operates as in the above described embodiments, with the coil 2020 not being energized during operation. Periodically, the coil 2020 is switched on with a polarity that opposes the magnetic polarization of the magnets in the tines, effectively reducing the field to a low enough value as to release any adhering magnetic particles. The coil 2020 is then de-energized, allowing the field of the tine-end magnets to predominate once more. If the field necessary to neutralize the field of the magnet elements 2014 and 2014' is so large as to actually de-magnetize the tine-end magnetic elements 2014, the field of the coil 2020 is reversed and increased to a level sufficient re-magnetize the magnet elements 2014 and 2014'.

The embodiment in which elements 2014 and 2014' are permanent magnets has the advantage that coil 2020 is not energized during the fluid measurements, thereby not interfering with these measurements, as by having parasitic resonances within its structure. Also, since the magnetization and de-magnetization phases can be very brief, a very large transient current can be passed through the coil 2020 without risking overheating and burning out its winding.

In the embodiment in which magnetic elements 2014 and 2014' are magnetized by the coil 2020, both elements 2014 and 2014' will be magnetized in the same direction, but are required to move in opposite directions in order that the resonator 2010 forces remain balanced. This requires that element 2014 be driven by a first set of coils 2022 and 2024, and element 2014' be driven by a second coil set 2022' and 2024', so that the polarities of both the excitation field may be made opposite for the two elements 2014 and 2014'.

Using a dedicated coil set to drive and sense each magnetic 2014 has the further advantage of permitting a greater excitation field strength and greater sensing sensitivity for the system 2010, so this method has advantages whether an aligned or anti-aligned tine-end magnet configuration is used.

Figure 24:
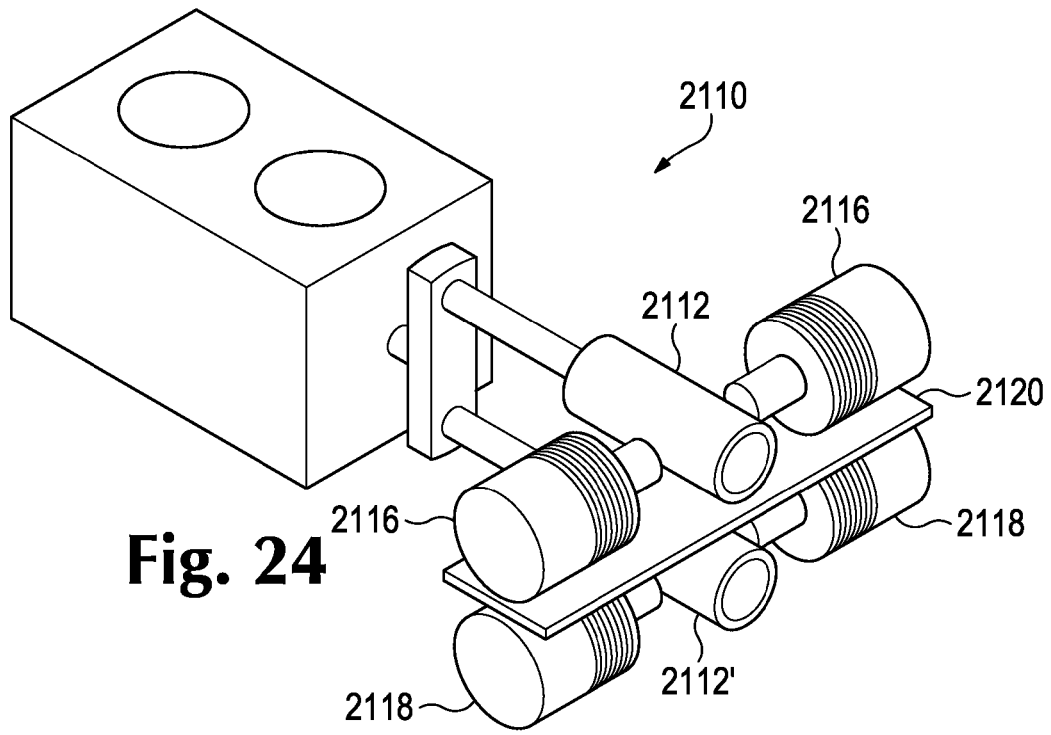
FIG. 24 is a perspective view of a preferred embodiment of a split drive/sense resonator assembly adapted to drive the tines in torsion, according to the present invention.

Resonator embodiment 2110 shown in FIG. 24 represents a departure from the prior art and the above described embodiment, in which the sense and excitation coils are wound coaxially. It is also possible, however, in the case of a tuning fork-type resonator to excite one tine, and sense the other, since both tines together form a single unitary resonator. Referring to FIG. 24, resonator 2110 includes a symmetrically disposed pair of torsional excitation coils 2116 around a first tine 2112, and similarly symmetrically disposed sense coils 2118 around the other tine 2112'. An electromagnetic shield 2120 is used to limit cross-talk or direct coupling between the sense coils 2118 and excitation coils 2116, thereby permitting continuous excitation and sensing of resonator 2110.

Figure 25:
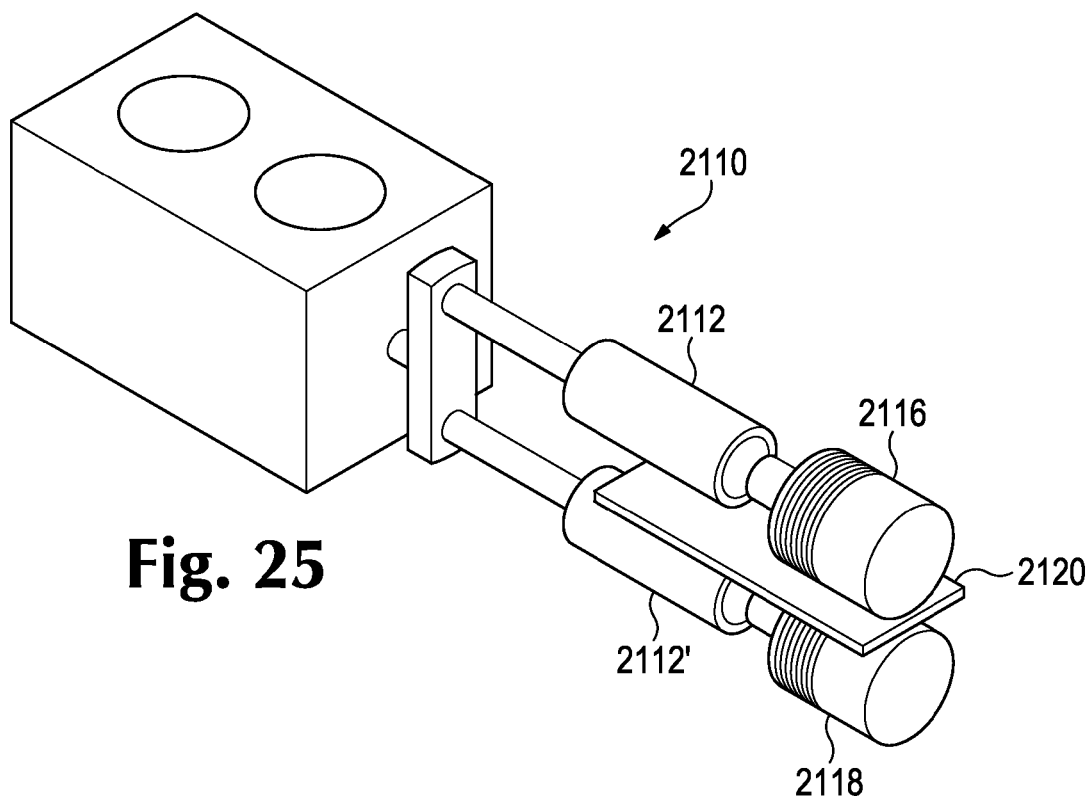
FIG. 25 is a perspective view of a preferred embodiment of a split drive/sense resonator assembly adapted to drive the tines in flexure, according to the present invention.

Referring to FIG. 25, in a further preferred embodiment 2210, adapted to resonate tines 2212 and 2212' in bending, excitation coil 2216 is positioned coaxially with first tine 2112 and sense coil 2218 is positioned coaxially with second tine 2112'.

Figure 26:
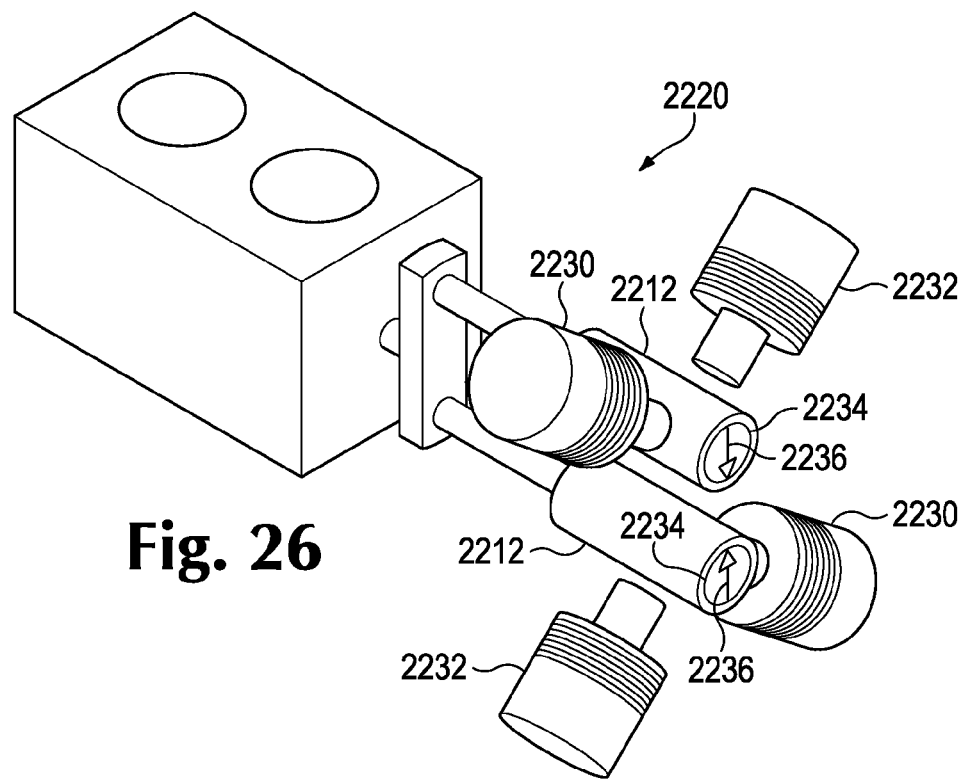
FIG. 26 is a perspective view of a preferred embodiment of a resonator assembly having torsion drive and sense coils that are mutually orthogonal, according to the present invention.

In a further preferred resonator embodiment 2220, shown in FIG. 26, the axes of the torsional sense coils 2230 and the axes of the excitation coils 2232 are placed at 90° to one another, with each coil axis 2230 and 2232 at 45° to a line coincident with the polarization vectors 2236 of the tine magnet 2234. Each excitation coil 2232 has a component perpendicular to the polarization vector 2236 of the tine-end magnet 2234, and each sense coil 2230 is responsive to the same component, but the polarization vectors of the fields produced by two neighboring coils 2230 and 2232 have no component in each other's directions, resulting in much-reduced crosstalk between the driving coils 2232 and sense coils 2230. This is advantageous should a continuous excitation and sensing scheme be used instead of the gated scheme. Similar arguments apply for the bending-mode excitation and sensing coils.

Figure 27:
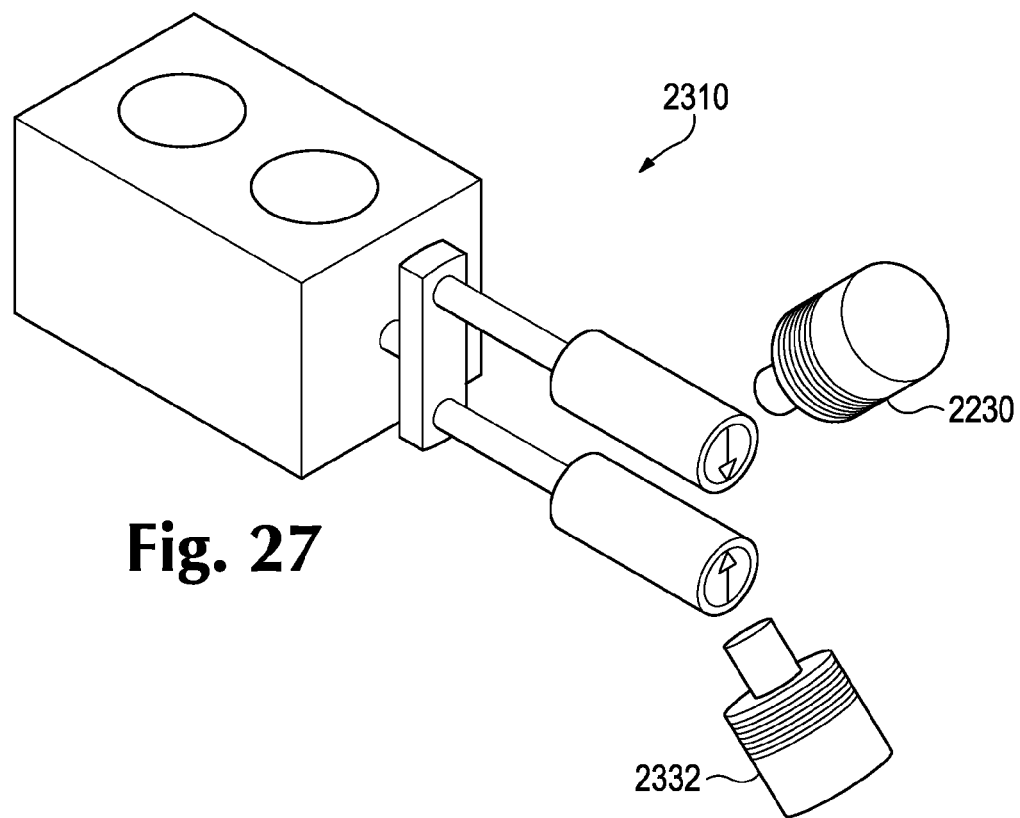
FIG. 27 is a perspective view of a preferred embodiment of a resonator assembly having flexural drive and sense coils that are mutually orthogonal, according to the present invention.

FIG. 27 shows a similar preferred resonator embodiment 2310, with a diagonally positioned sense coil 2330 and excitation coil 2332. Although these arrangements of coils with orthogonal axes are shown for use with a tuning fork-type resonator, their use is equally applicable to any other form of resonator, such as single rods, tubes, or re-entrant coaxial tube arrangements where it is of interest to reduce crosstalk between excitation and sensing coils, as when it is desirable to use continuous excitation and sensing. Prior art arrangements have used air-core excitation and sensing coils which, however, have relatively low electrical efficiency. Adding magnetically permeable cores to these coils can greatly improve both the generated field, in the case of the excitation coils, and the electrical sensitivity, in the case of the sensing coils. As will be discussed below, in the case of the excitation coils, which are typically driven by a controlled current source, this greatly increases the inductance of the coils, requiring greater voltage compliance from the current source in order to drive the inductance with minimal phase shifts. Possible core materials include soft iron, ferrites and similar materials. In the case of the excitation coils, soft iron or ferritic stainless steel (e.g. grade 430) is a good choice since these maintain their permeability up to substantially elevated field strengths. For the sensing coils, one of the high permeability alloys, like Permalloy, may be a good candidate, since it is exposed to relatively modest DC field strengths. The added inductance associated with a high-permeability core is negligible in the case of the sense coils because the preamplifier of the sensing circuitry can have a very large input resistance, which will render negligible the effect of the coil's inductive reactance is negligible. A further advantage to using a permeable core pertains to the case in which the coil needs to be separated physically from the resonator.

Figure 28:
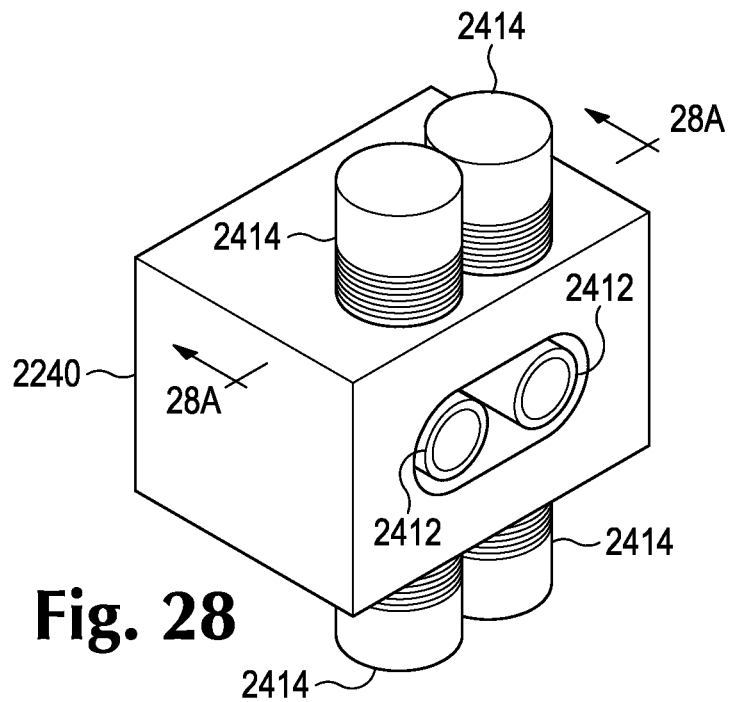
FIG. 28 is a perspective view of a preferred embodiment of a pressure cap resonator.
Figure 28A:
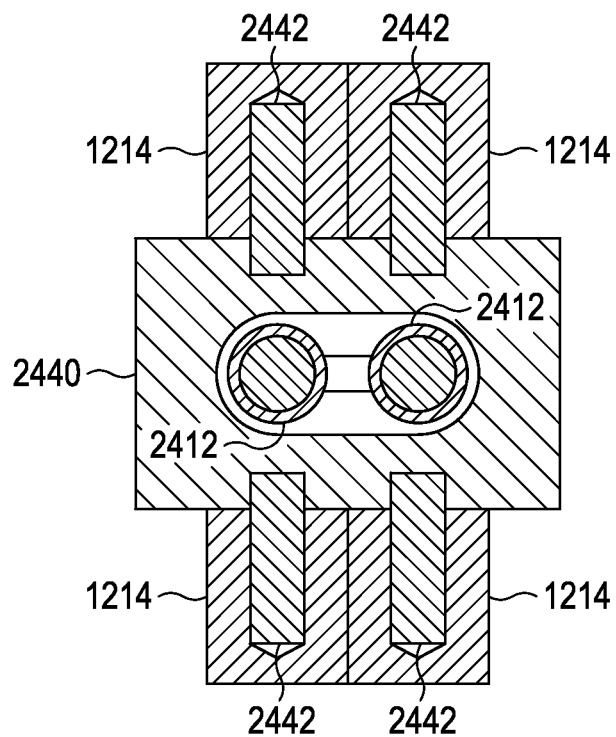
FIG. 28A is a sectional view of the pressure cap resonator of FIG. 27A.

Referring to FIGS. 28 and 28A, a preferred embodiment of a resonator assembly 2410 is adapted for use in sensing a fluid held at high pressure. A barrier 2440 separates a side adapted to be placed in high pressure, corrosive liquids, where tines 2412 are located, from a low pressure side where coils 2414 are located. Barrier 2440 must be permeable to a magnetic field and is, accordingly, made of austenitic stainless steel or a nickel alloy. To better contact the tines 2412 with the magnetic field, the coil's permeable cores 2442 (shown with coil windings removed, for clarity of presentation) extends through most of the barrier 2440, leaving a thin section of the barrier intact.

In the case that the barrier 2440 is composed of an austenitic stainless steel, or one of the austenitic nickel alloys, the magnetic cores 2442 of the coils 2414 are placed in a well that has been machined into the barrier 2440. The core 2442 is welded to the surface of the barrier 2440 furthest from the tines 2412, allowing the combination of the barrier 2440 and coils 2414 to function mechanically as a single unit. Austenitic alloys generally have very low magnetic permeability, and so cause minimal distortion of the field generated by the cores 2442 of coils, and do not appreciably shield the sense coil 2414 from the magnetic field created by movement of the tines 2412. As an alternative to welding, the magnetic cores 2442 may be pressed into slightly undersized holes in the barrier 2440, being retained by friction. In the case where the material comprising the barrier has a coefficient of thermal expansion equal to or less than that of the core, the elastic and frictional forces that hold the press-fit joint together will be maintained despite exposure to a large range of temperatures.

These foregoing measures result in a greatly increased electrical efficiency of the coil-and-resonator system, allowing the use of very weak magnets in the resonator itself. This can be highly advantageous from two viewpoints.

Weaker magnets are less likely to hold magnetic particles against the hydrodynamic forces of the fluid flowing by the resonator, which tend to sweep them away. And weaker magnets are more easily subject to demagnetization and remagnetization by an applied external field, as described above.

Figure 29:
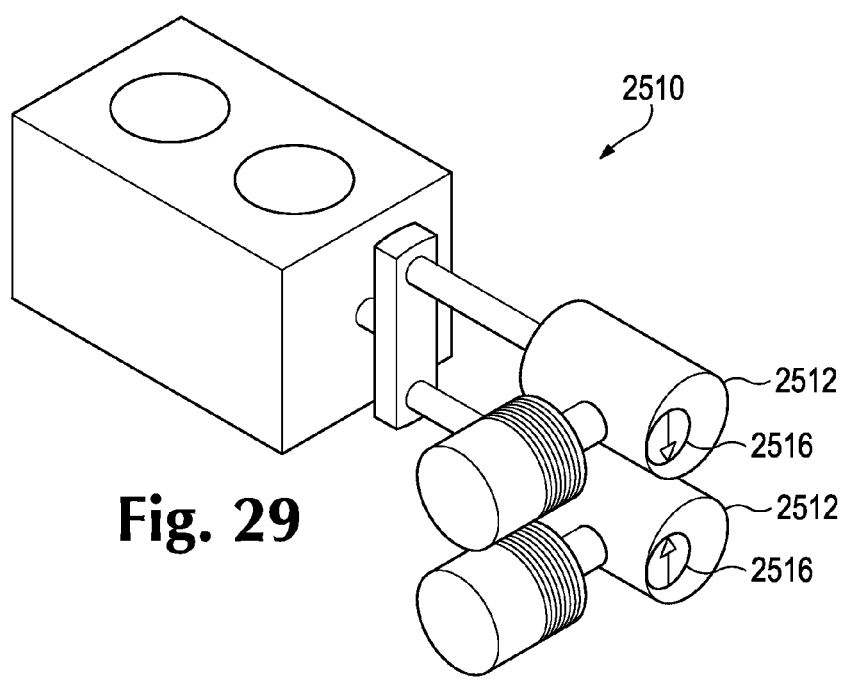
FIG. 29 is a perspective view of a resonator assembly having tine end magnets that are not concentrically mounted in the tines.

Referring to FIG. 29, a further preferred embodiment of a resonator 2510 reduces the total number of coils required for the tuning fork resonator operating in both torsional and bending modes. In the devices disclosed above, the tine-end magnets are shown to be coaxial with the tines. In resonator 2510, however, a pair of tine-end magnets 2516 are mounted eccentrically as shown in FIG. 29. Consequently, exciting a pair of tines 2512 in torsion will also induce a bending movement in the tines that will tend to make them vibrate in bending. If the frequency of excitation is that of the torsional mode, then the tines will vibrate in pure torsion, particularly if the density of the magnets 2512 is very close to that of the material making up the rest of the tines 2512. On the other hand, if the excitation frequency is that of the bending mode, the tines 2512 will vibrate in bending. Accordingly, resonator 2510 can function adequately, and form measurements of viscosity and fluid density with but a single pair of tines 2512.

The descriptions given above of resonator configurations are not meant to limit the scope of this invention, but merely to indicate one preferable embodiment. Further embodiments include, for example, exciting higher order torsional and/or bending modes in the tines of the resonator with the goal, for instance of obtaining more measurement data in a range of frequencies and shear rates that could contribute, for example, to a fuller rheological characterization of non-Newtonian fluids.

The invention claimed is:

1. A method for measuring the properties of a fluid, comprising:
   a. providing a torsionally resonant structure, including:
      i. a base structure;
      ii. at least two parallel tines affixed to said base structure and projecting in the same direction from said base structure; and
      iii. wherein said base structure is sufficiently compliant as to mutually couple said tines so that they behave as a single resonator when said tines are driven in synchronized manner, wherein said tines are driven in phase with one another and wherein said tines include magnets;
   b. providing a tine driving mechanism and tine movement sensing mechanism;
   c. immersing said resonant structure in said fluid;
   d. causing said tine driving mechanism to drive said tines torsionally;
   e. using said sensing mechanism to form measurements of tine movement response to said driving mechanism; and
   f. using said measurements of tine movement to form measurements of fluid properties.

2. The method of claim 1, wherein said magnets are permanent magnets.

3. The method of claim 1, wherein said magnets are electromagnets.

4. The method of claim 1, wherein said magnets are soft magnetic materials that can be magnetized by the presence of a superimposed magnetic bias field.

5. The method of claim 4, wherein said magnetic bias field is provided by permanent magnets.

6. The method of claim 4, wherein said magnetic bias field is provided by at least one electromagnet.

7. The method of claim 1, wherein the magnets are acted upon by an applied oscillating magnetic field, produced by said tine driving mechanism so as to cause the resonator to vibrate at a frequency in the proximity of its torsional resonant frequency.

8. The method of claim 7, wherein said oscillating magnetic field is provided by an electromagnet that is a component of said tine driving mechanism.

9. The method of claim 7, wherein said oscillating magnetic field is periodically interrupted in order to provide a sensing period in which said tine movement sensing mechanism is used to measure tine movement, without interference from said applied oscillating magnetic field.

10. The method of claim 7, wherein said oscillating magnetic field has at least a component perpendicular to the polarizations of said magnets.

11. The method of claim 1 wherein said tine movement sensing mechanism includes at least a sensing coil and an electronic amplification and analysis unit.

12. The method of claim 1, wherein said tines are substantially circular in cross section, whereby torsional movement of said tines shears said fluid.

13. The method of claim 12, further including the step of using said measurements of tine movement to form measurements of tine damping, which are used to form measurements of fluid viscosity.

14. The method of claim 1, further including:
 a. additionally to causing said driving mechanism to drive said tines torsionally, causing said driving mechanism to drive said tines to move flexurally through said fluid, displacing said fluid, which displaced fluid adds to the apparent mass of said tines, thereby causing its resonant frequency to change in response to fluid density, altering its resonant frequency; and
 b. causing said tine movement sensing mechanism to form measurements of tine movement in response to said driving said tines to move flexurally through said fluid.

15. The method of claim 14, wherein said driving of said tines alternates between torsional driving and flexural driving.

16. The method of claim 14, wherein said flexural driving and said torsional driving are simultaneous.

17. The method of claim 1, wherein said torsional driving of said tines is performed by applying a first oscillating magnetic field, oriented to drive said tines torsionally and oscillating at a frequency that causes the resonator to torsionally vibrate at a frequency in the proximity of its torsional resonant frequency, and applying a second magnetic field, oriented to cause said tines to vibrate in bending, and oscillating at a frequency that causes said tines to flexurally vibrate at a frequency in the proximity of one of their bending modes.

18. The method of claim 17, wherein said first oscillating magnetic field is provided by a first electromagnet, said first electromagnet so disposed as to drive said tines in at least in one of their torsional modes, said first electromagnet consisting of at least one coil.

19. The method of claim 17, wherein a second oscillating magnetic field is provided by a second electromagnet, said second electromagnet consisting of at least one coil.

20. The method of claim 17, wherein the oscillating magnetic fields are periodically interrupted in order to provide sensing periods in which sensing means can be used to monitor the response of the resonator without interference from the applied oscillating magnetic fields.

21. The method of claim 1, wherein the motion of the tines is sensed by sensing means that includes at least one sensing coil and an electronic amplification and monitoring unit.

22. The method of claim 1, wherein a first electromagnet is positioned to create a magnetic field having at least a component perpendicular to the polarizations of said magnets, said component acting to exert a torque on said magnets.

23. The method of claim 1, wherein said at least two parallel tines, includes:
 a. a pair of tines that are substantially circular in cross-section; and
 b. a pair of tines that are not circular in cross-section.

24. The method of claim 23, wherein said not-circular tines are rectangular in cross-section.

25. The method of claim 24, wherein said rectangular tines are square in cross-section.

26. A coupled resonator, comprising:
 a. a base structure having:
  a base stem having a base stem flexural elasticity per unit length;
  a base bridge; and
  a base neck connecting said bridge to said base stem, and having a flexural elasticity per unit length that is greater than that of said base stem;
 b. a plurality of tines having longitudinal axes, said axes being parallel to one another, all attached to and extending from said base structure in the same direction, each tine including:
  i. a narrow in transverse dimension tine stem portion;
  ii. a tine end wider in at least one transverse dimension than said tine stem portion, and having a tine end cross section;
  iii. a magnet held in said tine end.

27. The resonator of claim 26, wherein said base neck is sufficiently compliant to cause said tines to function as a single resonant unit.

28. The resonator of claim 26, wherein said base neck is sufficiently compliant to ensure decoupling said tines from said base stem.

29. The resonator of claim 26 wherein said tine stems have a circular cross section.

30. The resonator of claim 26 wherein said end portions of said tines are circular in cross section.

31. The resonator of claim 26, including driver means adapted to cause said tines to vibrate torsionally in the vicinity of one of their torsional resonances, and a sensing means to sense said torsional vibration of said tines.

32. A resonator assembly, comprising:
 a. a base structure;
 b. a first set of tines extending from said base structure in the same direction, each tine of the first set of tines having a portion that is not circular in cross-section;
 c. a second pair of tines extending from said base structure in the same direction, each tine of the second pair of tines being circular in cross-section;
 d. a driving mechanism, adapted to drive said tines in torsion; and
 e. a sensing mechanism, adapted to sense movement of said tines.

33. The resonator of claim 23 including driver means to cause said tines to vibrate torsionally in the vicinity of one of their torsional resonances, and a sensing means to sense said torsional vibration of said tines.

34. The resonator of claim 32, wherein said base structure includes:
 a. a base stem;
 b. a first base bridge, connected by a first base neck to said base stem, and from which said first set of tines extends;
 c. a second base bridge, connected by a second base neck to said base stem, and from which said second set of tines extends; and
 d. wherein said first base neck and said second base neck are more compliant than said base stem.

35. A resonator assembly, comprising:
 a. a torsionally resonant structure, including:
  i. a base;

ii. at least two parallel tines affixed to said base and projecting in the same direction from said base, each tine including a magnet; and
iii. wherein said base is sufficiently compliant as to mutually couple said tines so that they behave as a single resonator when said tines are driven in synchronized manner;
b. an electromagnetic drive assembly, comprising a set of electromagnetic coils positioned to drive said tines;
c. an electromagnet sense assembly, comprising a set of electromagnetic coils adapted to sense tine movement and being positioned orthogonally to said electromagnetic coils of said electromagnetic drive assembly.

36. A resonator assembly, comprising:
a. a torsionally resonant structure, including:
i. a base;
ii. at least two parallel tines affixed to said base and projecting in the same direction from said base, each tine including a tine magnet; and
iii. wherein said base is sufficiently compliant as to mutually couple said tines so that they behave as a single resonator when said tines are driven in synchronized manner;
b. an electromagnetic drive and sense assembly, comprising a set of electromagnetic coils positioned to collectively drive said tines and sense resultant tine movement, and wherein at least a subset of said electromagnetic coils at least used to drive said tines are positioned, relative to said tine magnets so that an oscillating magnetic field produced by said subset drives said tines in torsion.

37. The resonator of claim 36 wherein said tine magnets are set into said tines in a manner that is not concentric, whereby an oscillating magnetic field produced by said subset drives said tines in flexure as well as in torsion.

\* \* \* \* \*